United States Patent
Worrell et al.

(10) Patent No.: US 11,660,106 B2
(45) Date of Patent: May 30, 2023

(54) ARTICULATION JOINT HAVING AN INNER GUIDE

(71) Applicant: Cilag GmbH International, Zug (CH)

(72) Inventors: Barry C. Worrell, Centerville, OH (US); Randolph C. Stewart, Cincinnati, OH (US); Geoffrey S. Strobl, Williamsburg, OH (US)

(73) Assignee: Cilag GmbH International, Zug (CH)

( * ) Notice: Subject to any disclaimer, the term of this patent is extended or adjusted under 35 U.S.C. 154(b) by 1185 days.

(21) Appl. No.: 15/214,415

(22) Filed: Jul. 19, 2016

(65) Prior Publication Data

US 2018/0021051 A1 Jan. 25, 2018

(51) Int. Cl.
*A61B 17/068* (2006.01)
*A61B 17/29* (2006.01)
(Continued)

(52) U.S. Cl.
CPC .......... *A61B 17/285* (2013.01); *A61B 17/068* (2013.01); *A61B 17/2812* (2013.01); *A61B 17/29* (2013.01); *A61B 18/1445* (2013.01); *A61B 2017/00309* (2013.01); *A61B 2017/00323* (2013.01); *A61B 2017/2901* (2013.01); *A61B 2017/2905* (2013.01);
(Continued)

(58) Field of Classification Search
CPC .............................................. A61B 2017/2905
USPC ....................................................... 227/175.1
See application file for complete search history.

(56) References Cited

U.S. PATENT DOCUMENTS 5,704,534 A * 1/1998 Huitema .......... A61B 17/07207
  227/175.1
7,008,375 B2 * 3/2006 Weisel ................... A61B 17/29
  600/139

(Continued)

FOREIGN PATENT DOCUMENTS

CN 103445815 A 12/2013
EP 1621137 A2 2/2006

OTHER PUBLICATIONS

International Search Report and Written Opinion for International App. No. PCT/US2017/042440 dated Oct. 17, 2017 (17 pages).

*Primary Examiner* — Thanh K Truong
*Assistant Examiner* — Patrick B Fry
(74) *Attorney, Agent, or Firm* — Mintz Levin Cohn Ferris Glovsky and Popeo, P.C.

(57) ABSTRACT

Devices and methods for articulating a distal end of a surgical device are provided. In one exemplary embodiment, the device includes an articulation joint that includes both an inner guide and an outer sleeve. The inner guide includes one channel extending therethrough that receives both a cutting mechanism and a closure band. Further, an outer surface of the inner guide, in conjunction with the outer sleeve, can define two additional channels that each receive an articulation band for articulating an end effector coupled to the articulation joint. The outer surface of the inner guide can include a plurality of ribs that also help define the two additional channels. Further, the outer sleeve can include a plurality of slots formed in it to improve flexibility and stability. Additional configurations of articulation joints, and configurations of components of a surgical device, are also provided, as are methods for using the same.

27 Claims, 25 Drawing Sheets

(51) Int. Cl.
  *A61B 17/285* (2006.01)
  *A61B 17/28* (2006.01)
  *A61B 18/14* (2006.01)
  *A61B 18/00* (2006.01)
  *A61B 17/00* (2006.01)

(52) U.S. Cl.
  CPC ............... *A61B 2017/2927* (2013.01); *A61B 2018/00607* (2013.01); *A61B 2018/1455* (2013.01)

(56) References Cited

U.S. PATENT DOCUMENTS

| | | | |
|---|---|---|---|
| 7,857,183 B2 | 12/2010 | Shelton, IV | |
| 8,298,232 B2 | 10/2012 | Unger | |
| 8,795,306 B2* | 8/2014 | Smith | A61B 17/320758 |
| | | | 606/159 |
| 9,301,759 B2* | 4/2016 | Spivey | A61B 17/068 |
| 9,339,271 B2* | 5/2016 | Ranucci | A61B 17/10 |
| 2006/0025812 A1* | 2/2006 | Shelton | A61B 17/07207 |
| | | | 606/205 |
| 2007/0084897 A1 | 4/2007 | Shelton et al. | |
| 2007/0225562 A1 | 9/2007 | Spivey et al. | |
| 2011/0184459 A1 | 7/2011 | Malkowski et al. | |
| 2011/0295242 A1 | 12/2011 | Spivey et al. | |
| 2011/0319888 A1 | 12/2011 | Mueller et al. | |
| 2012/0078247 A1* | 3/2012 | Worrell | A61B 18/1445 |
| | | | 606/45 |
| 2012/0078248 A1* | 3/2012 | Worrell | A61B 18/1445 |
| | | | 606/45 |
| 2012/0083835 A1 | 4/2012 | Shelton, IV et al. | |
| 2012/0143175 A1 | 6/2012 | Hermann et al. | |
| 2012/0289773 A1 | 11/2012 | Joshi et al. | |
| 2013/0161374 A1 | 6/2013 | Swayze et al. | |
| 2014/0053940 A1 | 2/2014 | Konstorum et al. | |
| 2014/0239042 A1 | 8/2014 | Simms et al. | |
| 2015/0066022 A1 | 3/2015 | Shelton, IV et al. | |
| 2015/0088178 A1 | 3/2015 | Stolen et al. | |
| 2015/0173756 A1* | 6/2015 | Baxter, III | A61B 17/07207 |
| | | | 227/177.1 |
| 2016/0058441 A1 | 3/2016 | Morgan et al. | |
| 2016/0174976 A1* | 6/2016 | Morgan | A61B 17/072 |
| | | | 227/175.1 |
| 2016/0174983 A1* | 6/2016 | Shelton, IV | A61B 17/0644 |
| | | | 227/176.1 |

* cited by examiner

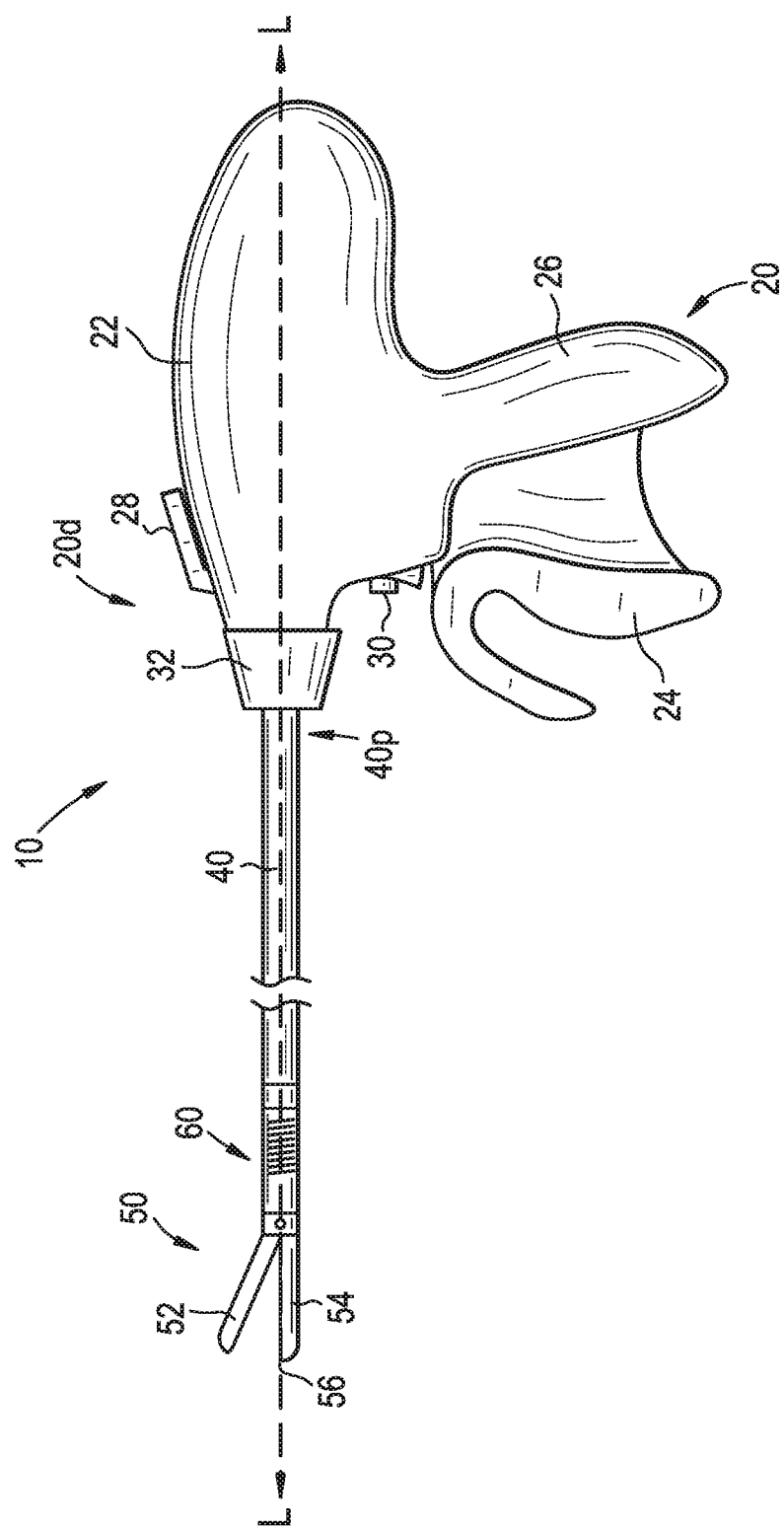

ARTICULATION JOINT HAVING AN INNER GUIDE

FIELD

The present disclosure relates to surgical devices and methods for grasping, cutting, and/or sealing tissue, and more particularly to improved devices and methods for articulating an end effector of such devices.

BACKGROUND

Surgical devices are used in various open, endoscopic, and laparoscopic surgeries to seal and transect tissue volumes and blood vessels. The devices generally include jaws for grasping tissue therebetween and a cutting mechanism that is advanced through the grasped tissue to transect it. In some instances the devices are configured to apply electrical energy to the grasped tissue to seal it before tissue transection is completed. For example, various mono-polar and bi-polar radio frequency (RF) surgical instruments and surgical techniques have been developed for sealing tissue volumes and blood vessels. Electrodes can be disposed on a face of one or both of the jaws and can apply energy to the grasped tissue to promote hemostasis.

Some such devices also include the ability to articulate a distal end of the device, such as the jaws, or more generally an end effector. An articulating distal end allows the jaws to be manipulated off a central longitudinal axis of the device to access, or at least more easily access, more areas of a surgical site than would otherwise be possible if the jaws were not articulable with respect to a shaft of the device. However, the ability to articulate an end effector has resulted in some complications with the device. In some instances, a location of the end effector with respect to a shaft of device can change due to the amount of force applied to a lower jaw when an upper jaw is closed. The strength of the articulation joint that allows for articulation may not be as strong as it may otherwise be if no articulation was designed into the device. Thus, for example, when a jaw assembly is closed, a pull force exerted on the jaw assembly to compress tissue can be approximately in the range of about 30 pound-forces to about 45 pound-forces, which can cause a lower jaw of the jaw assembly to be displaced from its location with respect to the shaft of the surgical device by about 0.25 inches.

In some instances, another complication is that a cutting mechanism, such as a cutting blade or knife, can get hung-up or even stuck in a channel extending through the device when the end effector is articulated. Likewise, articulation bands, which can be used to actuate the articulation of the end effector, can buckle during and after articulation, particularly on a push side when two articulation bands are used to push and pull the end effector in a particular direction. The failure on the push side can occur, for example, during a surgical procedure when a surgeon is manipulating tissue. The surgeon may articulate the end effector to a desired location and operate it to grasp tissue and/or push on tissue with the end effector in a direction that would de-articulate the joint, which in turn can cause the push side (i.e., the outside articulation band) to buckle because it is not properly supported. This can result in complete joint failure such that the device no longer articulates and is stuck in a single position. For example, joint ribs of the articulation joint may break out and fail.

Accordingly, there remains a need for strong, durable articulation joints that remain flexible and can withstand force applied to the joint by closing and/or articulating jaws of an end effector. The devices should be designed to minimize unintended movement of the end effector with respect to the shaft of the surgical device and enable articulation without concern that portions of the end effector or articulation joint will fail and/or not be operable in a particular articulated configuration.

SUMMARY

Devices and methods are generally provided for articulating an end effector of a surgical device in a manner that better distributes the load imparted on components of the device when the jaws are closed, and makes it easier for cutting mechanisms, closure bands, and articulation bands to move to perform their functions regardless of whether the end effector is in a straight configuration, a fully-articulated configuration, or in some other location between those two configurations. The devices provided for herein generally include an inner support member or guide that defines channels through which cutting mechanisms and articulation mechanisms can be disposed. The inner guide can help protect these components and their travel paths so they can more easily move between their most proximally retracted and most distally advanced positions throughout the course of use, whether the end effector of the device is articulated to any degree. An outer sleeve can be used in conjunction with the inner guide to help define some of the channels, such as those through which articulation bands can be disposed. The outer sleeve can have particular slot configurations formed therein that improve the ability of the device to articulate while allowing the other features of the device, such as the cutting mechanism, closure band, and articulation bands, to operate properly.

In one exemplary embodiment, the surgical device includes a housing, an elongate shaft extending distally from the housing, an articulation joint coupled to a distal end of the elongate shaft, and an end effector coupled to the articulation joint. The articulation joint includes both an outer sleeve and an inner guide that is disposed within the outer sleeve. The outer sleeve has a plurality of radially-extending slots formed in it. Each of the outer sleeve and the inner guide is coupled to the elongate shaft, and the combination of the outer sleeve and inner guide forms at least three separate channels that each extend a length of the inner guide. These channels include a first channel that is configured to receive an actuation member, a second channel that is configured to receive a first articulation arm, and a third channel configured to receive a second articulation arm. Each of the actuation member, the first articulation arm, and the second articulation arm extends from the housing, through the elongate shaft, and into the articulation joint. The end effector is configured to be actuated by the actuation member and articulated by the first and second articulation arms.

The inner guide can include an elongate body. The first channel that is configured to receive an actuation member can be formed in the elongate body. Further, the elongate body can include ribs formed on an outer surface of the body. For example, a plurality of first ribs can be disposed along a length of a first outer surface of the body and a plurality of second ribs can be disposed along a length of a second outer surface of the body, with the plurality of second ribs being disposed on an opposite side of the body than the plurality of first ribs. The plurality of first ribs and a portion of the outer sleeve can define at least a portion of the second channel and the plurality of ribs and another portion of the outer sleeve can define at least a portion of the third channel.

The plurality of first ribs can include a plurality of rows of first ribs, with one or more ribs having opposed first and second wings. The first and second wings can define a space between them that is part of the second channel. Likewise, the plurality of second ribs can include a plurality of rows of second ribs, with one or more ribs having opposed first and second wings. The first and second wings for the second ribs can define a space between them that is part of the third channel.

In some embodiments, two stiffening elements can be associated with the elongate body. For example, a first stiffening element can be coupled to a first inner wall of the elongate body and a second stiffening element can be coupled to a second inner wall of the elongate body, with the inner walls being opposed to each other on opposite sides of the first channel. As a result, the first and second stiffening elements can also be opposed to each other on opposite sides of the first channel. The first and second stiffening elements can include metal. Further, in some embodiments, a distal end of each of the first and second stiffening elements can extend distally beyond a distal terminal end of the elongate body of the inner guide and can be coupled to the end effector.

The radially-extending slots of the outer sleeve can include a plurality of rows of radially-extending slots with each row being disposed at a different location along a length of the outer sleeve. Further, each row can include at least a first radially-extending slot and a second radially-extending slot. In some embodiments, a distance between adjacent, opposed terminal ends of the first radially-extending slot and the second radially-extending slot is constant across the length of the outer sleeve. In some other embodiments, a distance between adjacent, opposed terminal ends of the first and second radially-extending slots at a proximal end of the plurality of rows of slots can be greater than a distance between adjacent, opposed terminal ends of the first and second radially-extending slots at an intermediate section of the plurality of rows. Similarly, a distance between adjacent, opposed terminal ends of the first and second radially-extending slots at a distal end of the plurality of rows of slots can be greater than the distance between the adjacent, opposed terminal ends of the first and second radially-extending slots at the intermediate section of the plurality of rows. In some embodiments, the terminal ends of the first and second radially-extending slots of the plurality of rows of radially-extending slots can be curved towards either or both of a proximal end and a distal end of the outer sleeve.

In some other embodiments, an outer sleeve can include a tubular body and two cage members. The tubular body can have a proximal portion, an intermediate portion, and a distal portion, with the intermediate portion having opposed support arms that extend between the proximal and distal portions. The first cage member can include a portion of the radially-extending slots that are formed in the outer sleeve, and the second cage member can also include a portion of the radially-extending slots that are formed in the outer sleeve. The first cage member can engage the opposed support arms and be coupled to the inner guide, while the second cage member can also engage the opposed support arms and be coupled to the inner guide, but be disposed on an opposite side of the opposed support arms than the first cage member.

One of the second and third channels can be configured to receive a wire that extends from the housing, through the elongate shaft, into the articulation joint, and to the end effector. The wire can provide power to the end effector, for example to power an electrode disposed on a surface of one or both jaws to seal tissue disposed between the jaws when the end effector includes jaws. In some embodiments, the end effector includes a first jaw and a second jaw. The first and second jaws can be configured to move relative to one another between an open position in which the jaws are spaced a distance apart from one another, and a closed position in which the jaws are configured to grasp tissue between them. A cutting blade can be disposed in the first channel and configured to advance through the first channel and through the first and second jaws to cut tissue grasped between them. In some embodiments, an insulative adapter is disposed between the elongate shaft and the articulation joint. The adapter can couple the articulation joint to the elongate shaft. It can also be configured to electrically isolate the end effector from the elongate shaft.

In another exemplary embodiment of a surgical device, the device includes a housing, an elongate shaft extending distally from the housing, an articulation joint coupled to a distal end of the elongate shaft, first and second articulation bands that each extends from the housing, through the elongate shaft, and into the articulation joint, a jaw assembly coupled to the articulation joint and each of the first and second articulation bands, and a cutting blade. The articulation joint includes an inner guide that has an inner channel formed in it, opposed stiffening elements disposed on opposed sides of a distal portion of the inner channel, and ribs disposed along a length of an outer surface of the inner guide. The inner channel is configured to receive the cutting blade. The ribs include a plurality of first ribs that are disposed along a length of a first outer surface of the inner guide and a plurality of second ribs that are disposed along a length of a second outer surface of the inner guide. The second ribs are disposed on an opposite side of the inner guide than the first ribs. The first ribs define at least a portion of a first outer channel for receiving the first articulation band, and the second ribs define at least a portion of a second outer channel for receiving the second articulation band. The second articulation band is on an opposite side of the inner guide than the first articulation band. The jaw assembly includes a first jaw and a second jaw that are pivotally coupled together to open and close for the purpose of grasping tissue between the jaws. The jaw assembly is configured to be articulated by the first and second articulation bands. More particularly, the jaw assembly is movable between a straight configuration and a fully-articulated configuration by the first and second articulation bands. The cutting blade is disposed in the inner channel formed in the inner guide and is configured to advance through at least a portion of the first and second jaws to cut tissue grasped between the jaws. The articulation joint is configured to allow the cutting blade to fully advance and fully retract when the jaw assembly is in any configuration between and including the straight configuration and the fully-articulated configuration.

In some embodiments, the articulation joint includes an outer sleeve that is disposed radially outward from the inner guide. The outer sleeve can define at least a portion of each of the first and second outer channels. In one non-limiting example of an outer sleeve, the sleeve includes a plurality of rows of slots that are formed in the sleeve. Each row can be disposed at a different location along a length of the outer sleeve, and each row can include at least a first slot and a second slot. In some such embodiments, a distance between adjacent, opposed terminal ends of the first slot and the second slot can be constant across the length of the outer sleeve. In some other such embodiments, a distance between adjacent, opposed terminal ends of the first and second slots at a proximal end of the plurality of rows of slots can be greater than a distance between adjacent, opposed terminal ends of the first and second slots at an intermediate section of the plurality of rows. Similarly, a distance between adjacent, opposed terminal ends of the first and second slots at a distal end of the plurality of rows of slots can be greater than the distance between the adjacent, opposed terminal ends of the first and second slots at the intermediate section of the plurality of rows. In some embodiments, the terminal ends of the first and second slots of the plurality of rows can be curved towards either or both of a proximal end and a distal end of the outer sleeve.

In another non-limiting example of an outer sleeve, the sleeve can include a tubular body and two cage members. The tubular body can have a proximal portion, an intermediate portion, and a distal portion, with the intermediate portion having opposed support arms that extend between the proximal and distal portions. Each of the first and second cage members can include a plurality of slots formed in it. The first cage member can engage the opposed support arms and be coupled to the inner guide, while the second cage member can also engage the opposed support arms and be coupled to the inner guide, but be disposed on an opposite side of the opposed support arms than the first cage member.

Each of the first and second stiffening elements can include metal. In some embodiments, a distal end of each of the opposed stiffening elements can extend distally beyond a distal terminal end of an elongate body of the inner guide to which the opposed stiffening elements are coupled, and the distal ends of the opposed stiffening elements can be coupled to the end effector.

The device can include an insulative adapter. The adapter can be disposed between the elongate shaft and the articulation joint to couple the articulation joint to the elongate shaft. The insulative adapter can be configured to electrically isolate the jaw assembly from the elongate shaft.

Methods of using the device to allow for articulation at any angle of articulation for an end effector are also provided. Exemplary embodiments are disclosed throughout the application or are otherwise derivable from the present disclosures. In one exemplary embodiment, a surgical method includes closing opposed jaws of a surgical device on tissue disposed between the jaws to grasp the tissue. The opposed jaws are coupled at their proximal end to a distal end of an articulation joint of the surgical device, and the articulation joint is coupled to an elongate shaft of the surgical device. Further, the articulation joint includes an outer sleeve and an inner guide that is disposed radially inward from the outer sleeve. The method further includes articulating the opposed jaws with respect to a central longitudinal axis that extends through the elongate shaft of the surgical device, and distally advancing a cutting mechanism through a channel extending through a length of the inner guide through at least a portion of the opposed jaws to cut the tissue disposed between the opposed jaws. The articulation joint is configured in a manner that allows the step of distally advancing a cutting mechanism through a channel formed in the inner guide to be performed regardless of the articulated configuration of the jaw assembly. Thus, the distal advancement of the cutting mechanism can occur when the jaw assembly is in a straight configuration, in a fully-articulated configuration, and in a partially-articulated configuration disposed between the straight configuration and the fully-articulated configuration.

In some embodiments, the step of closing the opposed jaws can include moving a closure band longitudinally through a channel that extends through a length of the inner guide to actuate one of the jaws with respect to the other. The channel of the inner guide through which the cutting mechanism extends can be the same channel through which the closure band extends.

The method can also include applying energy by way of an electrode associated with at least one of the opposed jaws to the tissue disposed between the opposed jaws. The inner guide can include one or more stiffening elements disposed in it. For example, opposed stiffening elements can be coupled to opposed inner walls of the channel extending through the inner guide. In some embodiments, the distal ends of the stiffening element(s) can be coupled to the proximal end of the opposed jaws.

An outer surface of the inner guide and the outer sleeve can define second and third channels of the inner guide. In such instances, the step of articulating the opposed jaws with respect to a central longitudinal axis extending through the elongate shaft of the surgical device can include distally advancing a first articulation band coupled to at least one of the opposed jaws through the second channel to cause the opposed jaws to be articulated in one direction away from the central longitudinal axis. Alternatively, or additionally, a second articulation band coupled to at least one of the opposed jaws through the third channel can be proximally retracted to cause the opposed jaws to be articulated in that one direction away from the central longitudinal axis.

BRIEF DESCRIPTION OF DRAWINGS

This disclosure will be more fully understood from the following detailed description taken in conjunction with the accompanying drawings, in which:

FIG. 1 is a side view of one exemplary embodiment of a surgical device;

DETAILED DESCRIPTION

Figure 2A:
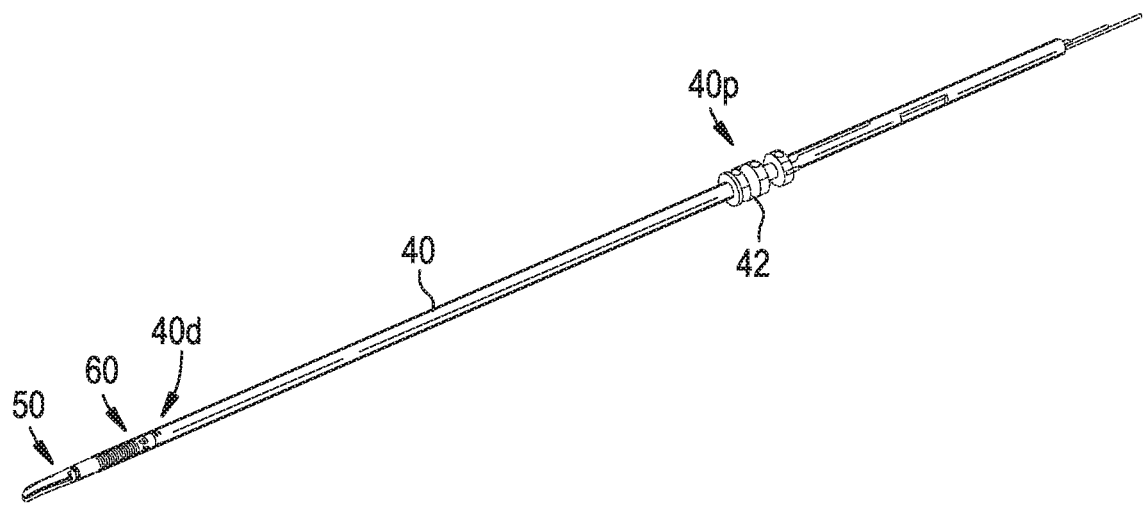
FIG. 2A is an isometric view of one exemplary embodiment of components of a surgical device for grasping, transecting, and sealing tissue, the device including a distal articulation end.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure. Further, in the present disclosure, like-numbered components of the various embodiments generally have similar features when those components are of a similar nature and/or serve a similar purpose. Additionally, to the extent features or sides of a structure are described herein as being a "first feature" or "first side" or a "second feature" or "second side," such numerical ordering is generally arbitrary, and thus such numbering can be interchangeable.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute. Further, a person skilled in the art will recognize that a number of different terms can be used interchangeably while still being understood by the skilled person. By way of non-limiting example, the terms "cut" and "transect" are generally used interchangeably herein.

The present disclosure generally relates to surgical devices and methods for articulating an end effector of a surgical device that allows the end effector to perform consistently regardless of how much the end effector is articulated with respect to an elongate shaft from which it is coupled to and/or extends. In the illustrated embodiments, the end effectors are jaw assemblies that are articulable with respect to an elongate shaft of the device, and the disclosures provide for features that allow the surgical device to grasp tissue with the jaws, cut tissue disposed between the jaws using a cutting mechanism that travels through the jaws, and seal the tissue disposed between the jaws using one or more electrodes associated with the jaws in any articulated configuration attainable by the device. The tissue with which the devices provided for herein can be used include tissue or blood vessels, collectively referred to herein as "tissue." The features provided for include an inner support member or guide that is designed to distribute the load imparted on components of the device when the jaws are closed, and also makes it easier for the cutting mechanisms, such as cutting blades or knifes, and articulation mechanisms, such as articulation arms or bands, to perform their functions in a straight or articulated configuration. The inner support member can be used in conjunction with an outer sleeve which can also help produce the aforementioned benefits.

FIG. 1 illustrates one embodiment of a surgical access device 10 configured to grasp, seal, and transect tissue. The surgical device can include a proximal handle portion 20, an outer elongate shaft 40, an end effector 50 for grasping tissue, and an articulation joint 60 for articulating the end effector 50 with respect to the outer elongate shaft 40. The handle portion 20 can be designed to operate various features of the end effector 50. For example, the handle portion can close and open a jaw assembly of the end effector 50 to grasp tissue. The jaw assembly can include jaws 52, 54 that are configured to pivot with respect to each other to grasp tissue disposed therebetween. By way of further non-limiting example, the handle portion 20 can initiate the supply of electrical energy to one or more electrodes 56 associated with either or both of the jaws 52, 54 to weld, coagulate, and/or seal portions of the grasped tissue. The components to initiate these actions can be part of the handle portion 20 and can extend through or be electrically or mechanically coupled to components that extend through the shaft 40. Components of this nature, such as a wire(s) or lead(s) 30 (FIGS. 2D and 2E), are known to those skilled in the art, and thus further elaboration related to the same is unnecessary. Further, the handle portion 20 can also be configured to operate other components that work in conjunction with the end effector 50, such as a closure band 84 (FIGS. 2D and 2E), opposed articulation bands 80, 82 (FIGS. 2C-2F), and a cutting mechanism 90 (FIGS. 2D and 2E), each of which extends through the shaft 40. As discussed in greater detail below, the closure band 84 is used to close the jaws, the articulation bands 80, 82 are used to articulate the jaws 52, 54 with respect to the shaft 40, and the cutting mechanism 90 is configured to cut tissue grasped by the jaws 52, 54. The wire 30, the closure band 84, the articulation bands 80, 82, and the cutting mechanism 90 are sometimes collectively referred to herein as the "end effector operational components."

Handle Portion

Figure 2B:
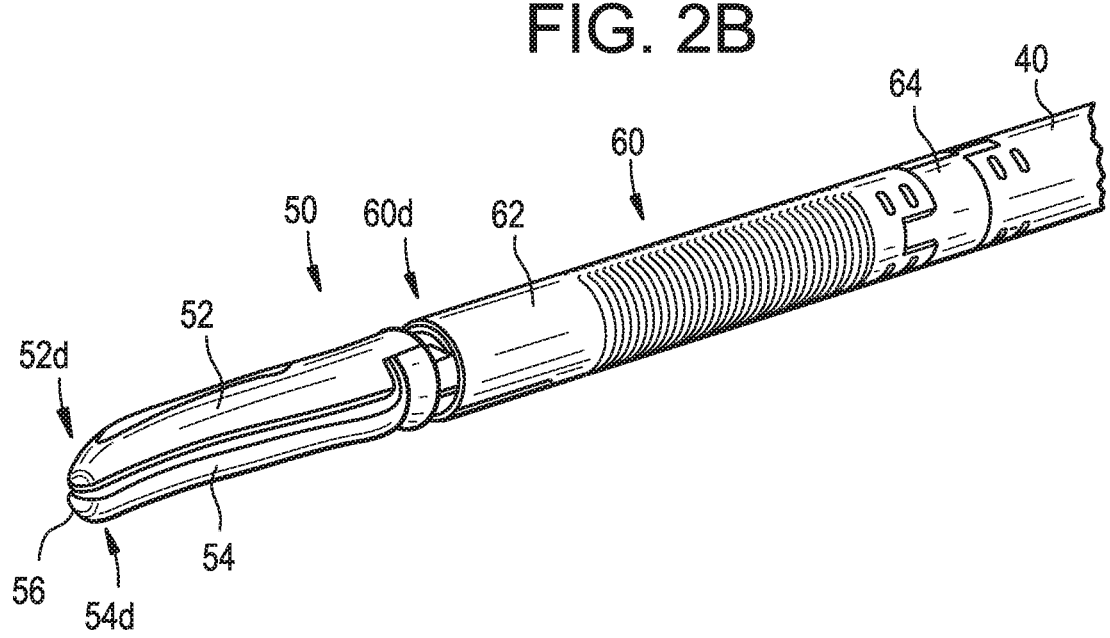
FIG. 2B is an isometric view the distal articulation end of FIG. 2A, the distal articulation end including an end effector and an articulation joint having an outer sleeve and an inner guide.

The handle portion 20 can have any type of design known in the art for operating end effectors 50. In the illustrated embodiment, the handle portion 20 has a pistol-grip configuration that includes a housing 22, an actuating handle or trigger 24, and a stationary handle 26. Movement of the actuating handle 24 towards the stationary handle 26 can be effective to perform a variety of functions. In the illustrated embodiment, the actuating handle 24 is effective to advance both the closure band 84 and the cutting mechanism 90. As the closure band 84 advances distally, a distal end 84d of the band 84 can include a pin 86 configured to be disposed in opposed slots 58 in one of the jaws 52, 54, as shown in FIG. 2D the upper jaw 52 (only one of which is visible), such that as the pin 86 advances distally, it engages a surface forming the slots 58 to close the jaws 52, 54 by advancing the upper jaw 52 towards the lower jaw 54. As the cutting mechanism 90 advances distally, it passes through the closed jaws 52, 54 to cut tissue disposed between the jaws 52, 54. The location of the closure band 84 with respect to the cutting mechanism 90 allows the jaws 52, 54 to be closed prior to the cutting mechanism 90 passing into the jaws 52, 54 to cut or transect tissue. The actuating handle 24 can be set-up such that as it returns to the initial position, i.e., as it moves away from the stationary handle 26, the cutting mechanism 90 and closure band 84 retract proximally. Alternatively, the actuating handle 24 can be set-up such that a second stroke is required to proximally retract the cutting mechanism 90 and closure band 84. In other embodiments, another control associated with the handle portion 20 can be operable to retract the cutting mechanism 90 and/or the closure band 84.

The handle portion 20 can also include an articulation handle or lever 28 for articulating the end effector 50. As shown, the articulation lever 28 can be disposed at a distal end 20d of the handle portion 20, for instance on a top portion of the handle portion 20. The lever 28 can be manipulated from side-to-side along a surface of the handle portion 20 (as shown, into and out of the page) to facilitate reciprocal articulation of the end effector 50. A person skilled in the art will recognize other configurations of an articulation lever, as well as other components that can be associated with a handle portion 20 to effect articulation of the end effector 50 in lieu of or in conjunction with the lever 28 without departing from the spirit of the present disclosure.

The mechanical and electrical components associating the closure band 84, articulation bands 80, 82, and cutting mechanism 90 with the actuating handle 24 and the articulation lever 28, respectively, can be disposed in the housing 22 and the outer elongate shaft 40, including drivers, controllers, and levers, among other components. For example, the driver can be a motor, such as a pneumatic motor, a hydraulic motor, and/or a solenoid, provided in the handle portion 20 and used to power any of the end effector operational components. Other designs that can be used to actuate the jaws 52, 54, the closure band 84, the articulation bands 80, 82, and/or the cutting mechanism 90 include but are not limited to actuator levers, triggers, and sliders. Further, a person skilled in the art will recognize other functions that the actuating handle 24 and/or articulation handle 28, or other means of actuation and articulation, can perform without departing from the spirit of the present disclosure.

The illustrated embodiment also includes an actuator, e.g. a button 30, as part of the handle portion 20. The button 28 can be configured such that pressing it completes a circuit to power the electrode(s) 56, via the wire 30, for instance by way of the driver, to seal tissue disposed in the jaws 52, 54. More particularly, completion of the circuit by the button 30 allows electrical energy to pass from a power source (e.g., the driver) disposed in the housing 22, through the wire 30, and to the electrode 56. The wire 30 can be disposed in the shaft 40 to electrically connect the button 30 and the electrode 56. Although the power source is described as being in the housing 22, in other embodiments the power source can be external of the housing 22 and the housing can be configured to electrically connect to the power source, for instance by way of a socket extending from the housing 22 to connect to the power source. Similar to the actuating handle 24, a person skilled in the art will recognize that the actuator 30 can have a variety of other designs, and can perform a variety of other types of functions, without departing from the spirit of the present disclosure.

Other features to assist in moving and actuating the components of the device 10 can also be incorporated into the handle portion 20. By way of example, the handle portion 20 can include a rotatable knob 32 disposed at a distal end 20d of the handle portion 20 to facilitate rotation of the shaft 40, and thus the end effector 50 coupled thereto, with respect to the handle portion 20 around a centrally disposed longitudinal axis L of the shaft 40. In the illustrated embodiment, the rotatable knob 32 is approximately adjacent to the articulation lever 28, although other locations for the components are possible. A person skilled in the art will recognize other non-limiting examples of features that can be incorporated with the handle portion 20 to assist in manipulating or otherwise operating the device include: (1) a retraction handle for retracting the cutting mechanism 90 towards and/or to its initial position in place of or independent of any retraction that is part of a firing stroke initiated by the actuating handle 24; (2) a firing lockout assembly to prevent the cutting mechanism 90 from being actuated at an undesirable time; and (3) an emergency return button to retract the mechanism 90 before a firing stroke is completed, for instance in a case where completing the firing stroke may cause tissue to be undesirably cut. Although features such as a retraction handle, a firing lockout assembly, and an emergency return button are not explicitly illustrated in the device 10, a person skilled in the art will recognize a variety of configurations for each feature that can be incorporated into the handle portion 20 and/or other portions of the device 10 without departing from the spirit of the present disclosure.

A person skilled in the art will recognize that to the extent the handle portion 20 is described or implies that a hand of a user operates the components thereof, the handle portion 20 can be configured such that its various components can be operated without a hand, for example through various electrical and/or robotic controls. As a result, the handle portion 20 may alternatively be referred to as a housing. Movement or other use of any and all of the end effector operational components, the jaws 52, 54, and the electrode 56 can be achieved by electrical and/or robotic controls.

Intermediate Portion of the Surgical Device

The outer elongate shaft 40 can be removably coupled to the distal end 20d of the handle portion 20 at a proximal end 40p of the shaft 40 and can include a bore (not visible) extending therethrough for passing mechanisms to help actuate the jaws 52, 54, or to perform other functions at the surgical site, such as cutting or delivering electrical energy for sealing. In the described embodiment, each of the end effector operational components are coupled to components of the handle portion 20 and extend through the bore formed in the shaft 40, into the articulation joint 60, and to the end effector 50. One or more components can be associated with the shaft 40 to assist in coupling the shaft 40 to the handle portion 20. As shown in FIG. 2A, a hub 42 is coupled to a proximal end 40p of the shaft 40 and an outer surface of the hub 42 is adapted to couple to a complementary surface formed inside the handle portion 20. The shaft 40, or another shaft, can extend proximally from the hub 42 and be configured to couple to the housing 22 so that the end effector operational components disposed therein can operated by various features of the handle portion 20.

A distal end 40d of the shaft 40 can be configured to receive the articulation joint 60 by any known means for coupling a component like the articulation joint 60 or an end effector to a shaft, including by a removable connection that allows various articulation joints to be removably and replaceably coupled to the distal end 40d based on the end effector with which the device is being used. While the shaft 40 can have any number of shapes and configurations, depending, at least in part, on the configurations of the other device components with which it is used and the type of procedure in which the device is used, in the illustrated embodiment the shaft 40 is generally cylindrical and elongate.

The configurations of the various components with which the shaft is used includes the end effector operational components. A person skilled in the art will be familiar with the various configurations for each of the cutting mechanism 90, the closure band 84, the articulation bands 80, 82, and the wire 30, and thus not much detail is provided herein.

Figure 2C:
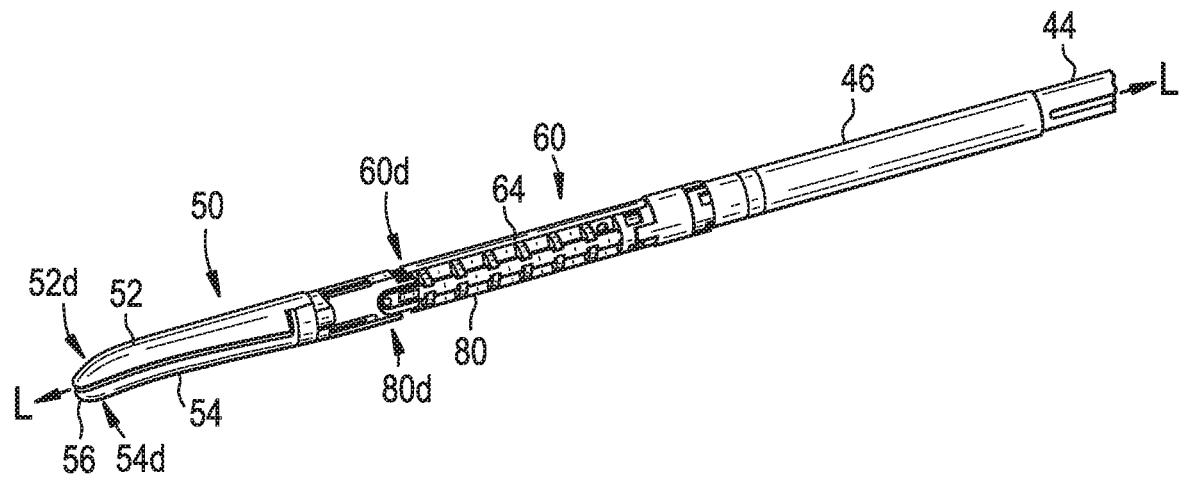
FIG. 2C is an isometric view of the distal articulation end of FIG. 2B with an outer elongate shaft of the device and the outer sleeve of the articulation joint hidden from view, thus illustrating upper and lower jaws of the end effector, the inner guide, an articulation band, an inner elongate shaft, and an insulative sleeve.
Figure 2D:
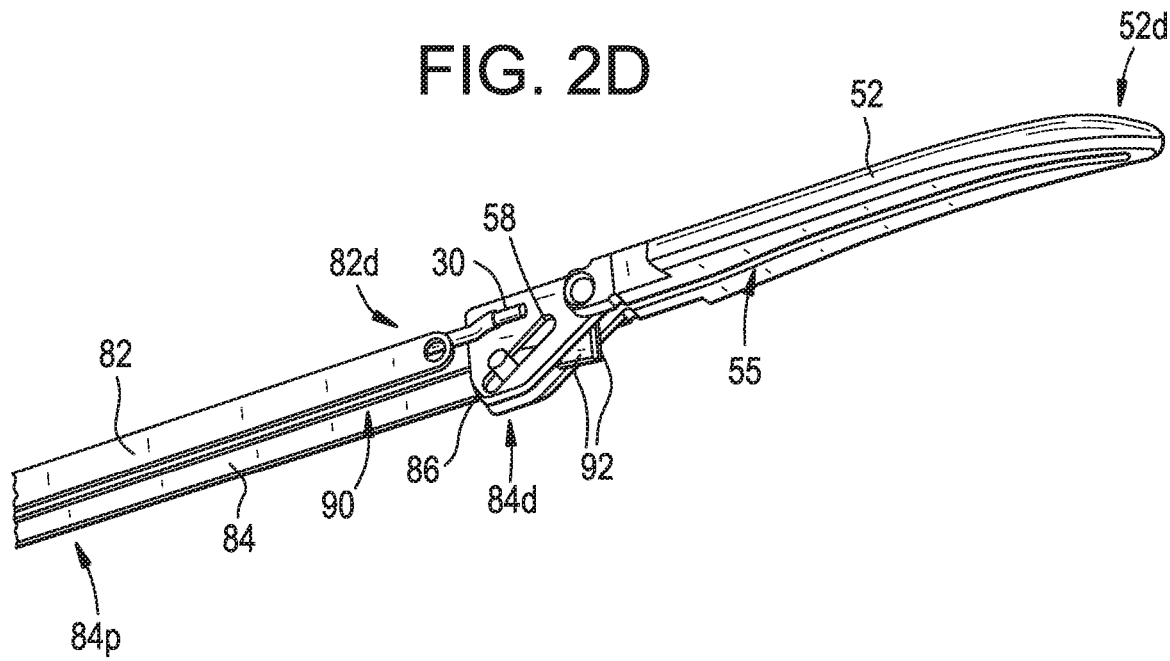
FIG. 2D is a side perspective view of the distal articulation end of FIG. 2C with the lower jaw and the inner guide hidden from view, thus illustrating the upper jaw, a cutting mechanism, a closure band, an articulation band, and a wire.
Figure 2E:
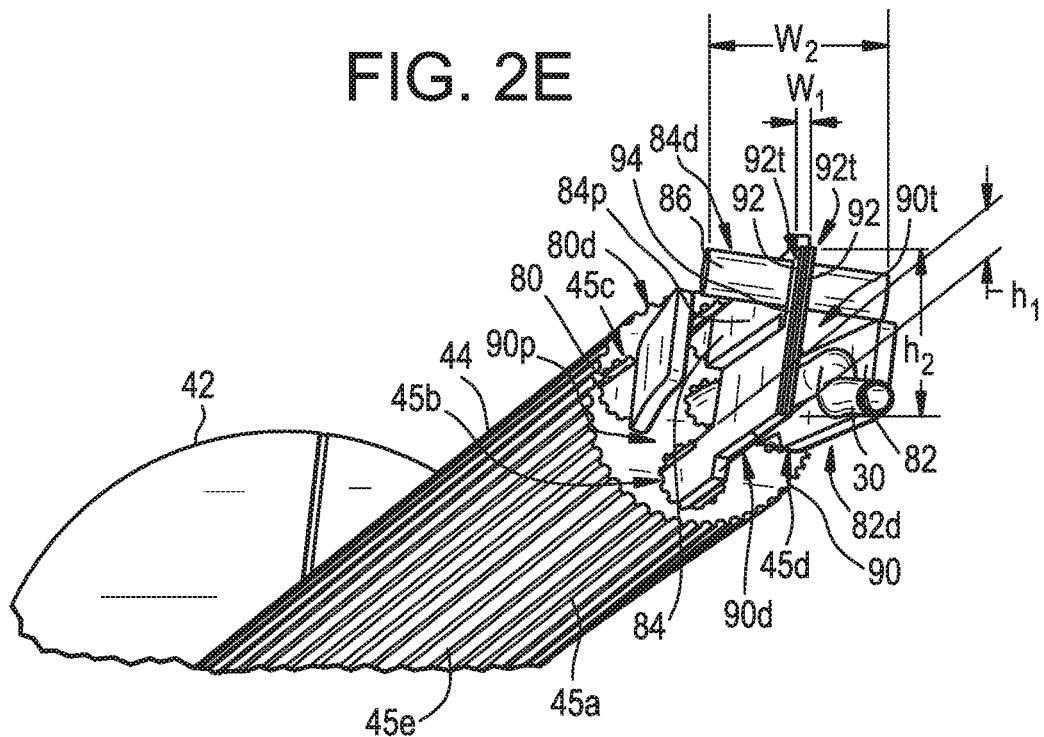
FIG. 2E is a front perspective view of the inner elongate shaft of FIG. 2C, the inner elongate shaft having the cutting mechanism, the closure band, the articulation band, and the wire of FIG. 2D, along with the additional articulation band of FIG. 2C, extending therethrough.

As shown in FIGS. 2D and 2E, the cutting mechanism 90 can be a plurality of drive beams 92 laminated or coupled together with a proximal portion 90p having a first height $h_1$ adapted for disposal in a desired location with respect to an inner shaft 44, and a distal portion 90d having a second, larger height $h_2$ adapted for passing through the jaws 52, 54 to cut tissue disposed therebetween. A distal tip 92t of the drive beams 92 can form a distal tip 90t of the cutting mechanism 90 that has a sharp edge conducive to cutting or transecting tissue. The distal portion 90d can also include a groove 94 complementary in shape to the closure band 84 so that the closure band 84 and cutting mechanism 90 can move in a complementary fashion. The cutting mechanism 90 may alternately be referred to as a cutting blade, a knife, or other terms known to those skilled in the art for describing a component that cuts or transects grasped tissue.

In the illustrated embodiment, the closure band 84 also has a proximal portion 84p having a height adapted for disposal in a desired location with respect to the inner shaft 44, and a distal portion 84d having a configuration that is adapted for other purposes. Rather than having a distal height that is substantially different from a proximal height though, it has a substantially different width at the distal portion 84d in comparison to the proximal portion 84p. The heights could, however, be substantially different if desired. More particularly related to the widths, a width $w_1$ at the distal portion 84d is substantially greater than a width w2 of the proximal portion 84p due to the pin 86 that is associated with the distal portion 84d. As described above, the pin is adapted to engage opposed slots formed in a jaw, e.g., the upper jaw as shown in FIG. 2D, such that proximal movement of the closure band pivots the upper jaw toward the lower jaw to move the jaws into a closed configuration, and distal movement of the closure band pivots the upper jaw away from the lower jaw to move the jaws into an open configuration. In other embodiments, the distal movement can move the jaws into the closed configuration and proximal movement can move the jaws into the open configuration. In other words, longitudinal movement of the closure band 84 can cause the opposed jaws to open and close, although other techniques for actuating jaws is also possible.

Each of the cutting mechanism 90 and the closure band 84 can advance between a fully retracted position and a fully advanced position. In the fully retracted position, the cutting mechanism 90 is retracted proximally towards the handle portion 20, but the distal portion 90d having the larger height does not extend into the inner shaft 44, and the closure band 84 is also retracted proximally towards the handle portion 20, with the pin 86 being disposed at proximal terminal ends of the slots 58 of the upper jaw 52. In the fully advanced position, the cutting mechanism 90 is advanced distally towards the end effector 50, with the distal tip 90t having passed substantially through the jaws 52, 54 such that it is proximate to or at distal terminal ends of the jaws 52. 54, and the closure band 84 is also advanced distally towards the end effector 50, with the pin 86 being disposed at distal terminal ends of the slots 58 of the upper jaw 52.

Figure 2F:
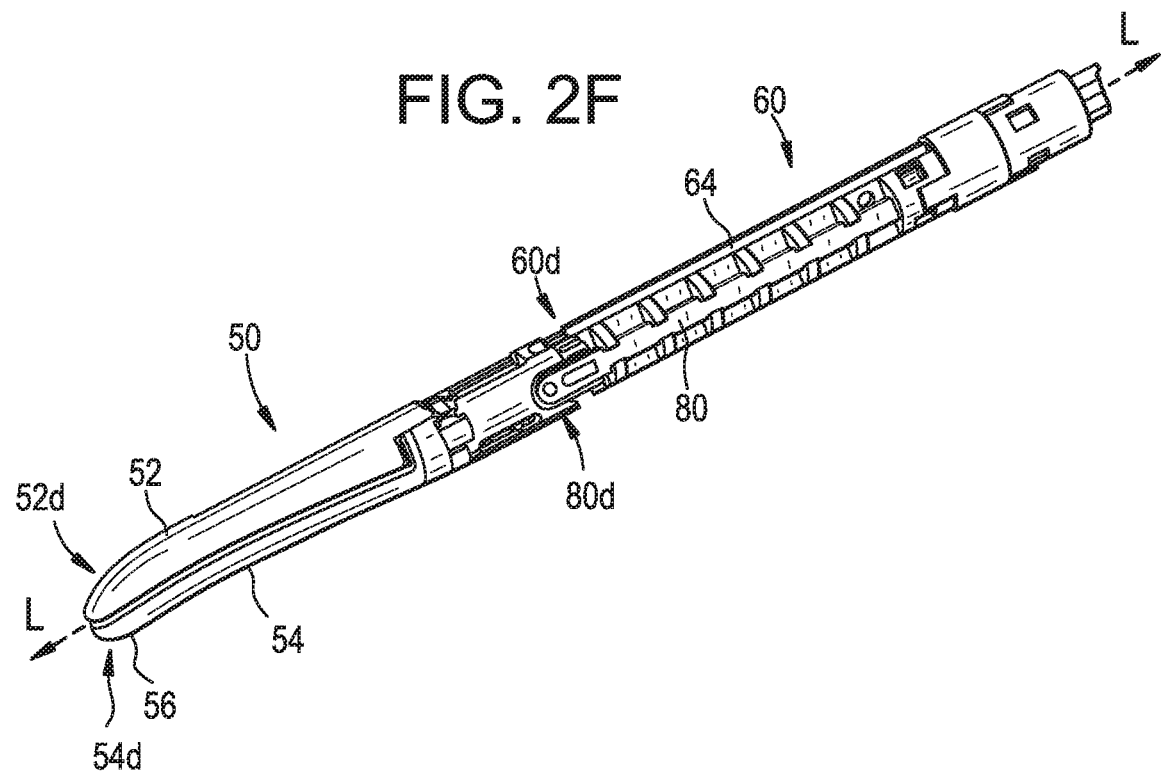
FIG. 2F is an isometric view of the distal articulation end of FIG. 2C with the inner elongate shaft and the insulative sleeve also hidden from view.
Figure 2G:
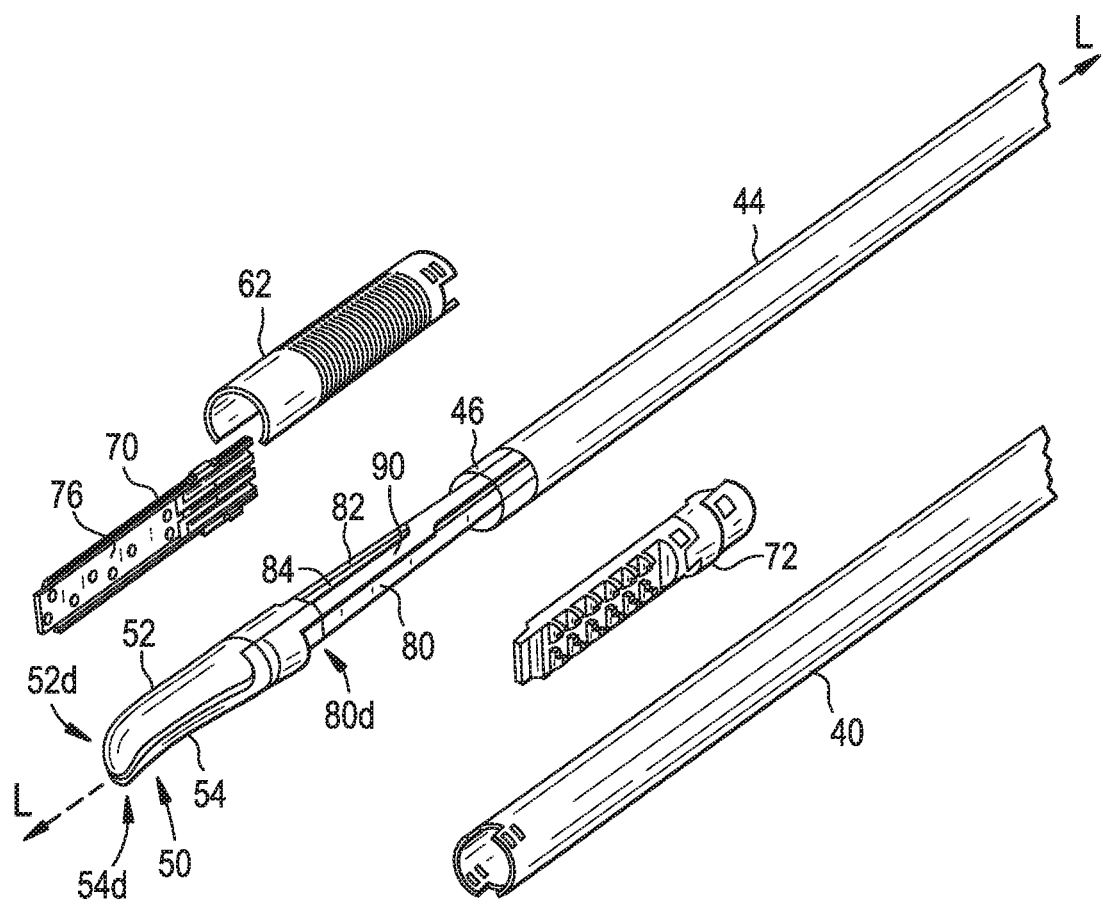
FIG. 2G is an exploded view of the distal articulation end of FIG. 2B.

The articulation bands 80, 82 can be disposed on opposed sides of the central longitudinal axis L of the outer shaft 40, approximately parallel thereto, with distal ends 80d, 82d thereof being coupled to one of the jaws, as shown in FIGS. 2C and 2F, the lower jaw 54. The end effector 50 is then articulated by selectively pushing and pulling the two articulation bands 80, 82 to manipulate the end effector 50 to the left or the right of the central longitudinal axis L. The components associated with the handle portion can be such that as the lever 28 is moved in one direction, e.g., left (out of the page with respect to FIG. 1) to articulate the end effector 50 to the left (out of the page with respect to FIG. 1), the articulation band 82 disposed on the right advances distally to push the end effector 50 to the left while the articulation band 80 disposed on the left retracts proximally to pull the end effector 50 to the left. The articulation bands 80, 82 can move the end effector 50 between a substantially straight configuration, which is often an initial configuration, in which a central axis of the end effector 50 is substantially aligned with the central longitudinal axis L of the outer shaft 40, to each of two fully-articulated configurations. In one fully-articulated configuration, the end effector 50 is articulated to the right (into the page with respect to FIG. 1) as far as the articulation band 80 can extend distally, i.e., the push state of the articulation band, and in the other fully-articulated configuration, the end effector 50 is articulated to the left (out of the page with respect to FIG. 1) as far as the articulation band 82 can extend distally, i.e., the push state of the articulation band. During articulation, when one band 80, 82 is in the push state, the other is typically in the pull state. In some embodiments, a range of articulation can be approximately 0 degrees in the substantially straight configuration to approximately 70 degrees off-center with respect to the central longitudinal axis L in either direction in the respective fully-articulated configurations. The end effector 50 can be articulated to any other angle or configuration between the substantially straight configuration and the fully-articulated configuration as desired, referred to herein as a partially-articulated configuration.

The wire 30 can also be provided. In the illustrated embodiment, it is configured to couple to the electrode 56 associated with the lower jaw 54. The wire 30 can be disposed at any location with respect to the inner shaft 40, and in some embodiments it can be isolated from the other end effector operational components.

As shown in FIGS. 2C and 2D, besides the end effector operational components, one or more additional tubes or shafts can be disposed within the outer elongate shaft 40. In the illustrated embodiment, an inner elongate shaft 44 is provided and is configured to individually receive one or more of the end effector operational components. The inner elongate shaft 44 can have the same central longitudinal axis L as the outer elongate shaft 40. As best shown in FIG. 2D, five separate lumens 45a, 45b, 45c, 45d, 45e (collectively lumens 45) are formed in the inner elongate shaft 44 along an entire length of the shaft 44, with each lumen 45 being configured to receive one of the end effector operational components. In the illustrated embodiment, a first lumen 45a receives the closure band 84 and a second lumen 45b disposed on an opposite side of the central longitudinal axis L from the first lumen 45a receives the cutting mechanism 90. Further, a third lumen 45c receives one articulation band 80 and a fourth lumen 45d disposed on an opposite side of the central longitudinal axis L from the third lumen 45c receives the other articulation band 82. As shown, the four lumens 45a, 45b, 45c, and 45d can be disposed circumferentially approximately equally around the inner shaft 44. In the illustrated embodiment, a fifth central lumen 45e that has a center that is the central longitudinal axis L is provided and is configured to receive the wire 30. As shown, the lumens 45 are sized to receive proximal portions of the end effector operational components, and at least some of them are sized such that a distal end of the end effector operational components cannot pass therethrough.

FIG. 2C illustrates an additional tube or sleeve, referred to herein as an insulative sleeve 46, that is coupled to each of the inner shaft 44 and an inner guide 64 of the articulation joint 60. The insulative sleeve 46 is generally cylindrical in shape, and provides electrical isolation to the outer elongate shaft 40.

End Effector

The end effector can have a variety of sizes, shapes, and configurations. In exemplary embodiments provided for in FIGS. 2A-2D, 2F, and 2G, an end effector 50 includes a first, upper or top jaw 52 and a second, lower or bottom jaw 54 disposed at the distal end 60d of the articulation joint 60. As shown, the second jaw 54 can be coupled to the distal end 60d of the articulation joint 60 such that it is relatively fixed with respect to the articulation joint 60, and the first jaw 52 is pivotally coupled to the lower jaw 54 to allow the jaws to be opened and closed with respect to each other. As described above, the upper jaw 52 can include opposed slots formed in a proximal end thereof such that distal and proximal movement of the closure band, and more specifically the pin disposed within the slots, results in the upper jaw pivoting closed and pivoting open, respectively. In an open configuration, the jaws 52, 54 can be spaced a distance apart from one another, while in a closed configuration the jaws are substantially opposed such that tissue engagement surfaces thereof are approximately parallel to each other and to the longitudinal axis $L_1$ extending through the shaft 40 and the end effector 50. A person skilled in the art will recognize that in other embodiments, the lower jaw 54 can pivot while the upper jaw 52 remains substantially stationary, or both jaws 52 and 54 can be pivotable with respect to each other.

In the illustrated embodiment, the jaws 52 and 54 have a substantially elongate shape with a slight curve along the longitudinal axis L at distal ends 52d and 54d of the jaws 52 and 54, but a person skilled in the art will appreciate that a variety of other shapes can be used to form the jaws 52 and 54, including jaws that are substantially elongate and substantially straight and configurations that are not necessarily congruent with respect to the opposed jaws across the duration of the length of the jaws. Further, the jaws 52 and 54 can have any suitable axial length for engaging tissue, where the axial length is measured along the longitudinal axis of the end effector 50. The axial length of the jaws 52 and 54 can also be selected based on the targeted anatomical structure for transection and/or sealing. Still further, the jaws 52 and 54 can also include an elongate channel 55 (FIG. 2D for the jaw 52; not illustrated for the jaw 54) extending between the two jaws to form a path through which the cutting mechanism 90 can traverse.

In some embodiments, the jaws 52 and 54 can have any combination of features configured to facilitate grasping tissue therebetween. For example, either one or both of the engagement surfaces of the jaws 52 and 54 can include one or more surface features formed thereon that can help secure the tissue thereon. The surface features can include, by way of non-limiting examples, teeth, ridges, or depressions configured to increase friction between the tissue and the engagement surfaces without tearing or otherwise damaging the tissue in contact with such surface features. A person skilled in the art will recognize that providing a plurality of teeth along an axial length of both engagement surfaces can facilitate grasping tissue and forming substantially smooth, uniform layers of tissue to improve tissue effect.

Additionally, one or both of the tissue engagement surfaces of the upper and lower jaws 52 and 54 can include one or more electrodes disposed thereon. As shown, the electrode 56 is disposed on the tissue engagement surface of the lower jaw 54 and is generally configured to supply energy to tissue disposed between the jaws 52 and 54 to coagulate or seal the tissue. The electrode 56 can be coupled to the tissue engagement surface of the jaw 54 using any manner known to those skilled in the art, including, by way of non-limiting example, using an adhesive. In some exemplary embodiments, the electrode 56 can made from a positive temperature coefficient (PTC) polymer or matrix that provides homogeneous and precisely regulated energy delivery with low thermal spread. The PTC conductive-resistive matrix can be a variably resistive body that comprises a polypropylene or a medical grade silicone polymer that is doped with conductive particles (e.g., carbon). Polymer PTC materials are known in the field of over current protection devices that will "trip" and become resistant when a selected trip current is exceeded. Although in the illustrated embodiments the electrode 56 is associated with only the lower jaw 54, in other embodiments, one or more electrodes can be disposed on only the upper jaw 52 or on both the upper and lower jaws 52 and 54. Likewise, any number of electrodes can be used on either jaw 52 and 54. In some embodiments, no electrodes are provided and the surgical device is designed to grasp tissue and not necessarily to seal or coagulate the grasped tissue.

Furthermore, and more generally, the illustrated embodiment of the surgical device 10 provides one of many different configurations, and associated methods of use, that can be used in conjunction with the disclosures provided herein. A variety of other configurations of a surgical device are also possible. For example, in some embodiments the device can be configured to apply staples to tissue in addition to or in lieu of either or both of cutting or sealing features. Some, non-limiting examples of other device configurations that can be used in conjunction with the present disclosure, and their related methods of use, include the disclosures provided for in U.S. Pat. No. 8,298,232, U.S. Patent Application Publication No. 2012/0083835, and U.S. Patent Application Publication No. 2013/0161374, each of which is incorporated by reference herein in its entirety. Further, in embodiments in which an end effector is not a jaw assembly, the closure band can more generally be referred to as an actuation member, with the actuation member being configured to cause the action for which the end effector is designed to perform to be performed. A person skilled in the art, in view of the end effector associated with the surgical device, can determine suitable actuation members to be used in place of a closure band. Further, to the extent a closure band is described herein, an actuation member can also be used, for example, in instances in which the end effector is not a jaw assembly.

A First Articulation Joint

The articulation joint 60 is disposed between the outer elongate shaft 40 and the end effector 50 and is configured to help the end effector 50 move at angles with respect to the central longitudinal axis L of the elongate shaft 40 and the end effector 50 so that the end effector 50 can be articulated to any position between the substantially straight configuration and either of the two fully-articulated configurations. The articulation joints provided for herein allow the load from closing the jaws together to be distributed more evenly across the joints, and decreases the possibility of any of the cutting mechanism, the closure band, and the articulation bands from buckling, getting caught up, or otherwise failing as the end effector is moved to and between different articulated configurations and the substantially straight configuration. The articulation joints provided for herein discuss both an inner guide and an outer sleeve, although in some embodiments only one of these components may be included as part of the articulation joint. For example, the inclusion of an inner guide as described herein can provide at least some of the desired benefits described throughout this application. Likewise, at least some of the benefits described with respect to the outer sleeve can also be attained in some instances with an inner guide.

The First Articulation Joint—Outer Sleeve

Figure 3A:
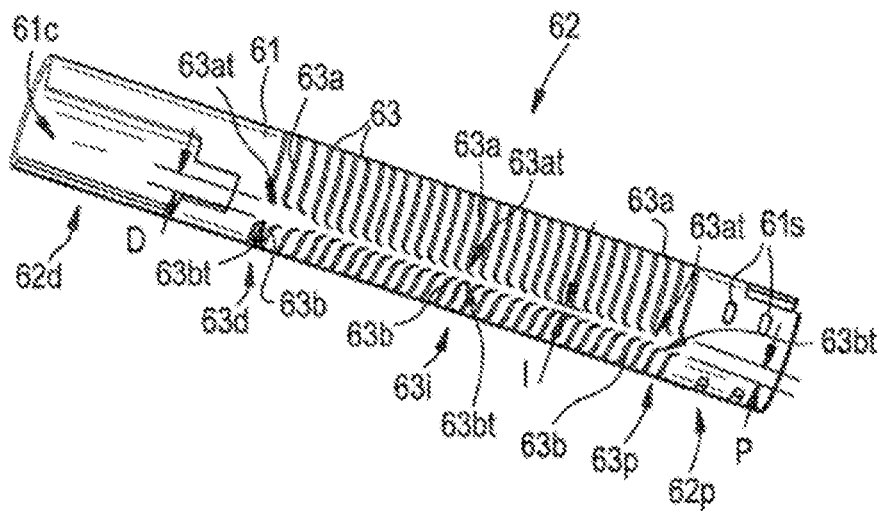
FIG. 3A is a bottom perspective view of the outer sleeve of the articulation joint of FIG. 2B.
Figure 3B:
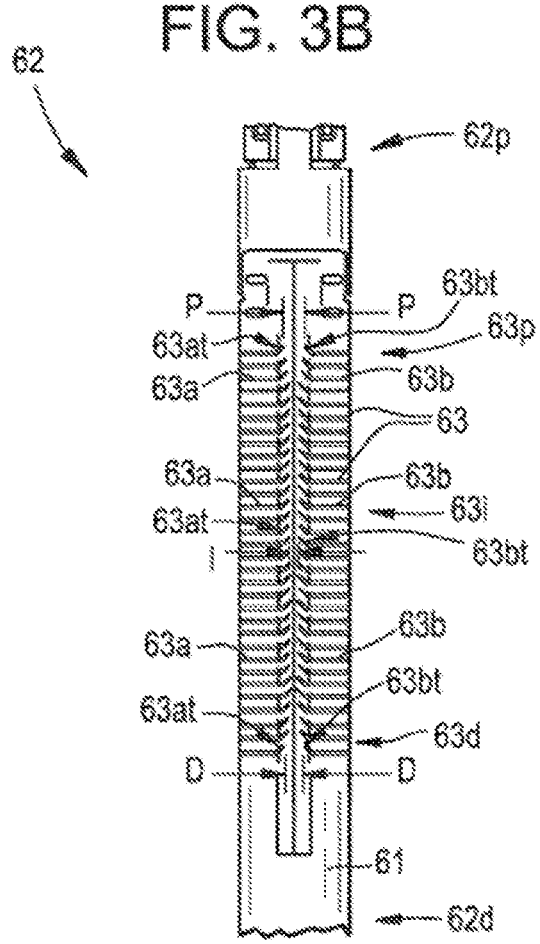
FIG. 3B is a top view of the outer sleeve of FIG. 3A.

The articulation joint 60 can include an outer sleeve 62 that is configured to provide flexibility to allow the end effector 50 to be articulated. One exemplary embodiment of the outer sleeve 62 is illustrated in detail in FIGS. 3A and 3B. As shown, the outer sleeve 62 is substantially cylindrical in shape and includes a plurality of slots 63 formed in an outer surface 61 of the sleeve 62. Additionally various mating features can be formed in the outer sleeve, such as slots 61s formed in a proximal end 62p of the sleeve 62. The sleeve 62 can also be shaped so that it can be snap fit onto various components of the device 10 with which it engages, or as described below, it can be welded, e.g., laser, or otherwise mated to one or more components of the device 10. A cut-out 61c formed in a distal end 62d of the sleeve 62 can allow for the pivot of a proximal end of the upper jaw 52 during opening and closing.

The plurality of slots 63 formed in the outer sleeve 62 can have a variety of configurations. In the illustrated embodiment, a plurality of rows of slots are formed in the outer surface 61, with each row being disposed at a different location along a length of the outer sleeve 62. Further, in the illustrated embodiment each row includes two radially-extending slots 63a, 63b, with a majority of a length of the slots being substantially parallel to counterpart slots in the other rows and substantially parallel to terminal ends 62ti, 62t2 of the outer sleeve 62. As shown, terminal ends 63at, 63bt at both ends of each slot 63a, 63b can be curved towards the proximal end 62p of the sleeve 62. The slots 63 can extend through an entire thickness of the outer sleeve 62, or alternatively, they may only extend through a portion of the thickness. Some slots may extend further through the thickness of the outer sleeve 62 than others.

Further, a distance between opposed terminal ends 63at, 63bt of the slots 63a, 63b in the same row can change across the length of the outer sleeve 62. In the illustrated embodiment, a distance P disposed between opposed terminal ends 63at, 63bt of the first and second slots 63a, 63b at a proximal end 63p of the plurality of rows of slots 63 is greater than a distance I disposed between opposed terminal ends 63at, 63bt of the first and second slots 63a, 63b at an intermediate section 63i of the plurality of rows of slots 63. Likewise, a distance D disposed between opposed terminal ends 63at, 63bt of the first and second slots 63a, 63b at a distal end 63d of the plurality of rows of slots 63 is greater than the distance I. In the illustrated embodiment, the distances P and D are substantially similar such that the a first half of the plurality of rows of slots 63 is substantially a mirror image of the second half of the plurality of rows of slots 63. The resulting configuration can be considered a bilateral bend configuration. In other embodiments, the distances I, P, and D can be approximately the same across the length of the outer sleeve 62. The distances I, P, and D can have a variety of values, and thus any of the three distances can be approximately in the range of about 0.008 inches to about 0.100 inches. In some exemplary embodiment, the distances P and D are about 0.070 inches and the distance I is about 0.015 inches, and in some other exemplary embodiments, the distances P and D are about 0.30 inches and the distance I is about 0.016 inches.

The slots 63 themselves can also have a variety of thicknesses, and a distance between slots in a same column along a length of the outer sleeve 62 can be similar or change over the course of the length. In some exemplary embodiments, a thickness of the slots 63 themselves can be approximately in the range of about 0.0008 inches to about 0.020 inches, and in some embodiments it can be about 0.004 inches. Further, in some exemplary embodiments an amount of space or distance between slots in a same column can be approximately in the range of about 0.010 inches to about 0.050 inches, and in some embodiments it can be about 0.021 inches. Similar to changing the distance between adjacent slots, i.e., slots in two different columns, as described with respect to the distances D, I, and P, changing the amount of space or distance between slots 63 in the same column along a length of the outer sleeve 62 and/or changing a thickness of the slots 63 can help control bend locations and a degree of articulation, which can also be referred to as a radius of curvature in any instance herein in which articulation is discussed. The changes in slot thickness and/or changes in the amount of space between slots in the same column can be done uniformly, or can be varied over the course of the length of the sleeve 62.

A person skilled in the art will recognize that the overall configuration of slots formed in the outer sleeve 62 can vary in many aspects without departing from the spirit of the present disclosure. For example, any number of rows can be formed, and they can be formed along any portion of the length of the outer sleeve 62. Likewise, each row can include any number of slots, including one or more than two. Still further, in other embodiments, terminal ends of the slots may not be curved, or only some may be curved, and the curve can be in any direction, including towards the distal end of the outer sleeve. The material to make the outer sleeve 62 can be generally stiff, with the slots 63 providing the desired flexibility. Some examples of exemplary materials for the outer sleeve 62 include metals, such as 304 stainless steel, Nitinol, titanium, and carbon-reinforced polymer extrusion. The slots 63 can be formed using a variety of techniques, including but not limited to laser cutting.

As shown in FIGS. 2A and 2B, the proximal end 62p of the outer sleeve 62 can be coupled to at least one of the elongate outer shaft 40 and the insulative sleeve 46, and the distal end 62d of the outer sleeve 62 can be coupled to the end effector 50. As discussed below, alternatively, or additionally, the outer sleeve 62 can be coupled, e.g., laser welded, to an inner guide 64 of the articulation joint 60.

The First Articulation Joint—Inner Guide

Figure 4A:
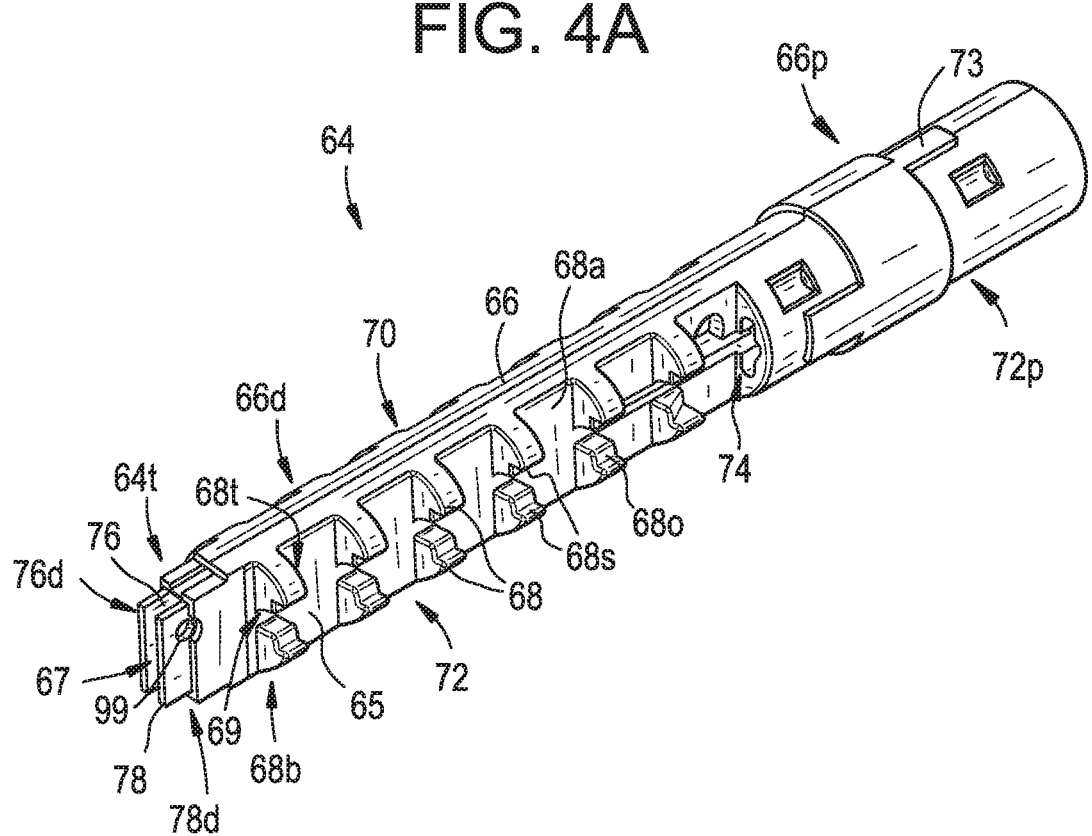
FIG. 4A is an isometric view of the inner guide of FIG. 2C.
Figure 4B:
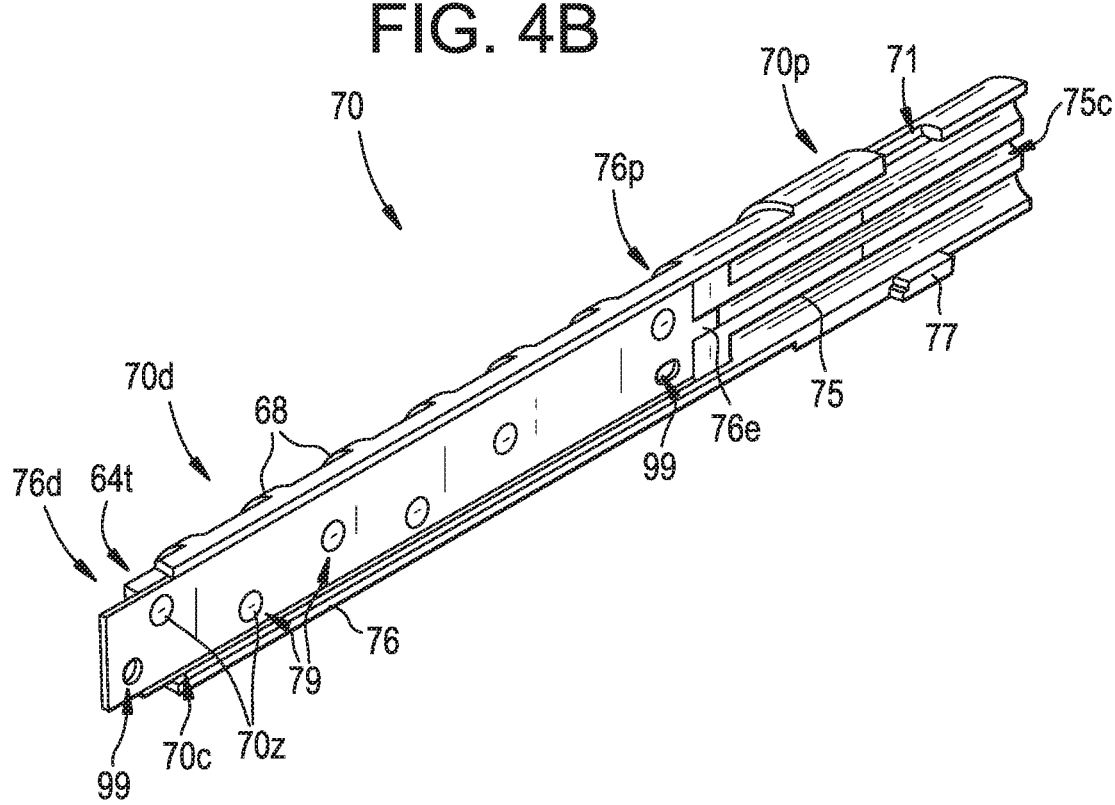
FIG. 4B is an isometric cross-sectional view of the inner guide of FIG. 4A taken along the line A-A.
Figure 5:
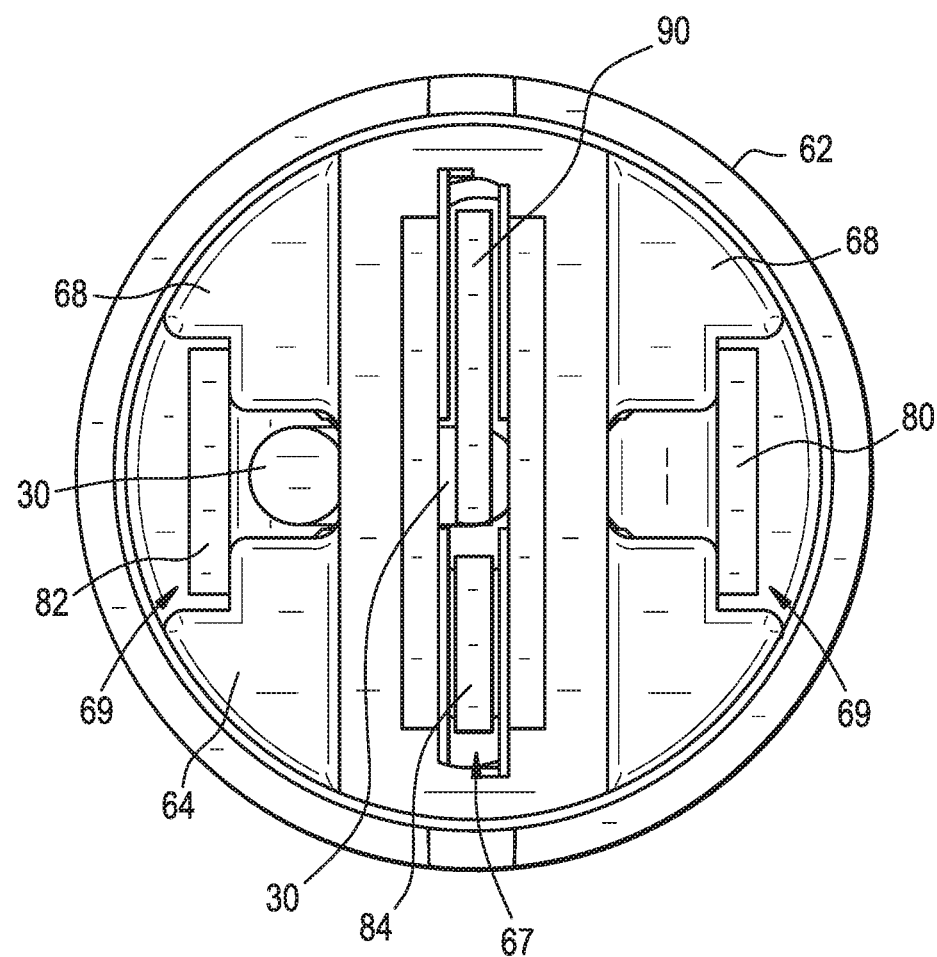
FIG. 5 is a front cross-sectional view of the articulation joint of FIG. 2B taken along the line B-B.

The articulation joint 60 can also include an inner support member or guide 64 that is configured to distribute the load that results from the jaws 52, 54 being closed and/or articulated, while also providing the flexibility to allow for articulation of the jaws 52, 54. As discussed herein, it is designed in a manner that allows the end effector operational components to be fully operational no matter how articulated or straight the end effector 50 is with respect to the elongate shaft 40. One exemplary embodiment of the inner guide 64 is illustrated in detail in FIGS. 4A and 4B, and in combination with the outer sleeve 62 in FIG. 5. As shown, the inner guide 64 includes an elongate body 66 that has a proximal portion 66p that is substantially cylindrical and a distal portion 66d that is substantially rectangular with ribs 68 disposed on opposed first and second sides of an outer surface 65 of the body 66, also referred to as first and second outer surfaces. The ribs 68 can be considered a part of the outer surface 65, for instance by being formed on or from the same material as the elongate body 66, or alternatively, they can be separate components attached to the outer surface 65. A central lumen or channel 67 is disposed in the body 66 and is configured to receive both the cutting mechanism 90 and the closure band 84, while the ribs 68 can help define lumens or channels 69 through which the articulation bands 80, 82 pass. Any of the lumens or channels 67, 69 can also be adapted to receive the wire 30, or alternatively, another lumen or channel can be formed within the inner guide 64 to pass the wire 30 therethrough. One such example is illustrated in FIG. 5, in which the wire 30 is disposed in the channel 69 defined by the inner guide 64 and outer sleeve 62 that receives the articulation band 82. The wire 30 can move from its channel 45e formed in the inner shaft 44 and towards the channel 67, as illustrated by the location of the wire 30 being behind a portion of the cutting mechanism 90 in FIG. 5.

In the illustrated embodiment, the inner guide 64 is made up of two complementary bodies 70, 72 that are coupled together to form the inner guide 64. One such body 70 is illustrated in FIG. 4B, with its outer surface being similar to the outer surface of the complementary body 72 that is visible in FIG. 4A. An outer surface of the proximal portion 70p has an arcuate shape to provide the cylindrical shape of the inner guide 64, while an outer surface of a distal portion 70d can be substantially rectangular and substantially flat with a plurality of the ribs 68 disposed on, formed on, or coupled to the substantially flat surface. In the illustrated embodiment, the ribs 68 are disposed along a length of the outer surface 65. As shown, each rib 68 can include a top wing 68t and a bottom wing 68b that help define the channel 69 that is designed to receive the articulation bands 80, 82. More particularly, each of the first and second wings 68t, 68b includes opposed, facing surfaces 68s that extend substantially perpendicular to the outer surface 65 on which the wings are disposed, and outwardly facing surfaces 68o that extend substantially parallel to the outer surface 65 onto which the wings 68t, 68b are disposed. As illustrated in FIGS. 2C, 2F, and 5, portions of these surfaces help define the channel 69 in which the articulation bands 80, 82 are received. A lumen 74 formed in the proximal portion 66p (FIG. 4A) can also define a portion of the channel 69 that receives the articulation bands 80, 82.

One or more coupling features can also be formed on the outer surface of the body. As shown in FIG. 4B, a female coupling member 71 is disposed on the proximal portion 70p of the body 70, which can be complementary to a male coupling member 73 disposed on a proximal portion 72p of the body 72, as shown in FIG. 4A. Alternatively, or additionally, coupling features can also be formed on an interior surface of the inner guide body, such as a male coupling member 77 disposed on an internal surface 75 of the proximal portion 70p illustrated in FIG. 4B. A complementary female coupling member can be disposed on the opposed surface of the other body 72.

The internal surface 75 of the body 70 can also include a channel 70c formed in the distal portion 70d. As shown, the channel 70c can be substantially rectangular in shape such that when the two bodies are mated together, the rectangular channel 67 is formed by the opposed first and second inner walls (not visible because obstructed by stiffening elements 76, 78) of the first and second bodies 70, 72 that are approximately parallel to each other. The rectangular channel 67 can receive the cutting mechanism 90 and the closure band 84.

The channel 70c can also be configured to receive a stiffening element 76. Accordingly, a depth of the channel 70c can be complementary to a thickness of the stiffening element 76 such that the stiffening element 76 does not interfere with the travel path of the cutting mechanism 90 or the closure band 84. As shown in FIG. 4A, each body 70, 72 includes a stiffening element 76, 78, respectively, associated with the respective inner walls that also define the channel 67. Thus, the stiffening elements 76, 78 are also substantially parallel to each other. Any technique known to those skilled in the art can be used to couple the stiffening elements 76, 78 to the respective inner walls. In the illustrated embodiment, a plurality of bosses 70z are formed on the inner walls to receive complementary lumens 79 formed in the respective stiffening elements 76, 78. The stiffening elements 76, 78 can then be associated with the bosses 70z using an injection molding processes in which the stiffening elements 76, 78 are placed in respective molds that include the bosses 70z and plastic is molded around the bosses 70z such that in use, for instance when the device is articulated, the stiffening elements 76, 78 stay attached to the elongate body 66. Further, the lumens 79 can be defined by surfaces having a bit of a rougher edge so the bosses 70z can more easily mate with the surfaces. In other embodiments the stiffening elements 76, 78 can be snap fit onto the bosses 70z and/or the bosses 70z can be melted and hardened to secure the location of the stiffening elements 76, 78 to the respective inner walls.

One or more manufacturing lumens 99 can be formed on one or both of the body 64 and respective stiffening elements 76, 78 to aid in manufacturing so that the components can be held at a particular location while the pieces are being assembled, for instance by locating pins. In the illustrated embodiment, two such lumens 99 are formed in the stiffening element 76 and one is formed in the elongate body 64, the proximal one of the two on the stiffening element 76 being aligned with the one formed in the elongate body 64. The distal lumen 99 of the stiffening element 76 can be positioned distal of a terminal end 64t of the elongate body 64 when the stiffening element 76 is positioned in the designated location with respect to the body 64 so it can be accessed during manufacturing. The bosses 70z and complementary lumens 79 of the stiffening element 76 can be disposed at any location and in any configuration, and thus the illustrated locations are by no means limiting.

The stiffening elements 76, 78 can have a variety of shapes and sizes, depending, at least in part, on the sizes, shapes, and configurations other components with which it is being used (e.g., the sizes, shapes and configurations of the inner guides) and the desired stiffness to be provided. In the illustrated embodiment the stiffening elements 76, 78 are substantially rectangular and are complementary in shape to the channels 70c, 72c (not shown) formed in the inner surfaces of the bodies 70, 72. As described above, a plurality of lumens 79 can be formed in the stiffening elements 76, 78. Further, one or more other mating features can also be provided to assist in positioning the stiffening elements 76, 78 in their designated bodies 70, 72, respectively. For example, a proximal end 76p can include an extension 76e that extends proximally from the main body of the stiffening element 76 and can be complementary in shape to a channel 75c formed in the internal surface 75 of the body 70 such that the extension 76e engages the surface 75 to assist in maintaining the stiffening element 76 in the internal guide 64. Exemplary materials for making the inner guide 64 include polymers, such as polycarbonate, polyetherimide (e.g., Ultem®), nylon, acrylonitrile butadiene styrene (ABS), or other similar polymers, and exemplary materials for making the stiffening elements 76, 78 include metals, such as 304 stainless steel, Nitinol, titanium, and other metals having a substantially higher modulus of elasticity in comparison to the polymers used for forming the inner guide 64.

The inner guide 64 can be coupled to the outer sleeve 62 to thereby couple it to each of the elongate shaft 40 and the end effector 50. For example, a portion of the inner guide 64 can be ultrasonically welded to the outer sleeve 62, which in turn can create a continuous, substantially monolithic configuration with the elongate shaft 40, the articulation joint 60, and the end effector 50. Alternatively, the inner guide 64 can be coupled directly to one or both of the elongate shaft 40 and the end effector 50. For example, the proximal portion 66p can include mating features that are complementary to mating features formed on the elongate shaft 40, and either the distal portion 66d or a distal end 76d, 78d of the stiffening elements 76, 78 can be configured to mate to the end effector 50. As illustrated, the outer sleeve 62 is disposed radially outward from the inner guide 64 or in the alternative, the inner guide 64 is disposed radially inward from the outer sleeve 62.

A Second Articulation Joint

Another exemplary embodiment of an articulation joint 160 for use in a surgical device is illustrated in FIGS. 6A-11. The articulation joint 160 provides similar benefits as described above with respect to the articulation joint 60. It also includes both an outer sleeve 162 and an inner guide 164, with the outer sleeve 162 including a tubular member or body 161 and two cage members 196, 197. The articulation joint 160 is designed to be disposed between, and thus coupled to, each of an elongate shaft 140 and an end effector 150. Other components of a surgical device, such as, by way of non-limiting examples, articulation bands, a cutting mechanism, a closure band, an insulating sleeve, and a handle portion and/or housing, can also be provided as part of the device. Further, in some embodiments only one of the outer sleeve 162 and the inner guide 164 may be included as part of the articulation joint 160.

The Second Articulation Joint—Outer Sleeve

The outer sleeve 162 of the articulation joint 160 is configured to provide flexibility to allow the end effector 150 to be articulated. In the illustrated embodiment, the outer sleeve includes both a tubular member or body 161 and two cage members 196, 197 that are mounted to or otherwise coupled with the tubular member 161.

Figure 7:
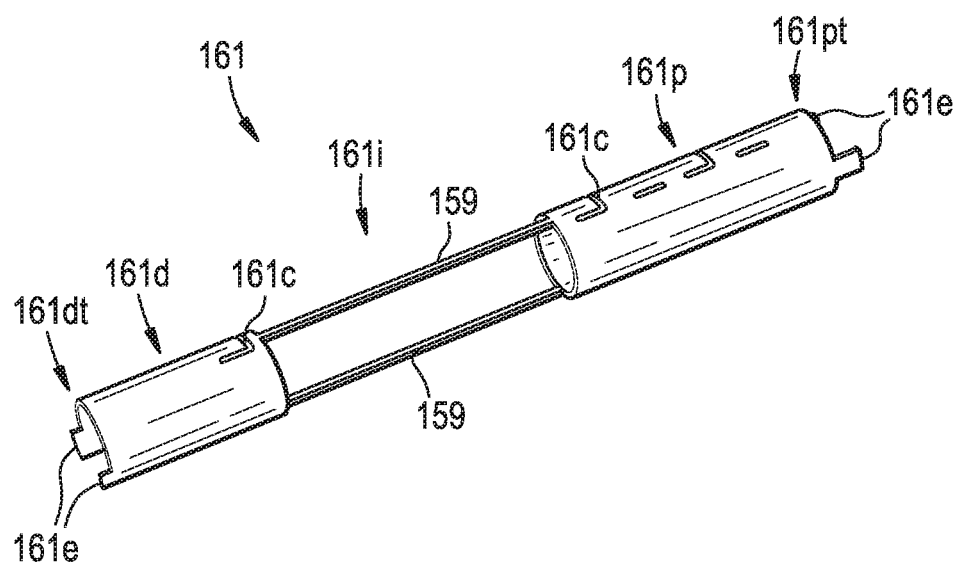
FIG. 7 is an isometric view of a tubular body of the outer sleeve of FIG. 6A.

FIG. 7 illustrates the tubular member 161, which includes a proximal portion 161p, an intermediate portion 161i, and a distal portion 161d. The proximal and distal portions 161p, 161d are substantially cylindrical in shape, with the intermediate portion 161i including opposed support arms 159 that extend between the proximal and distal portions 161p, 161d. The support arms 159 can be rails have a thickness similar to that of the proximal and distal portions 161p, 161d, and can be formed, for example, by cutting away opposed sides of an intermediate section of a cylindrical member. One or more crimp slots 161c can be formed in an outer surface of the proximal and/or distal portions 161p, 161d of the tubular member 161. In the illustrated embodiment, a plurality of U-shaped crimp slots 161c are formed and assist in mating the tubular member 161 with the inner guide 164 using techniques known to those skilled in the art. Slots of the nature described above with respect to the outer sleeve 62, i.e., the slots 63, can also be formed in the outer surface of the tubular member 161. Extensions 161e disposed on a proximal terminal end 161pt of the tubular member 161 can be complementary to recesses formed in an outer elongate shaft (not shown). Similarly, extensions 161e disposed on a distal terminal end 161dt of the tubular member 161 can be complementary to recesses formed in the end effector 150.

Figure 8A:
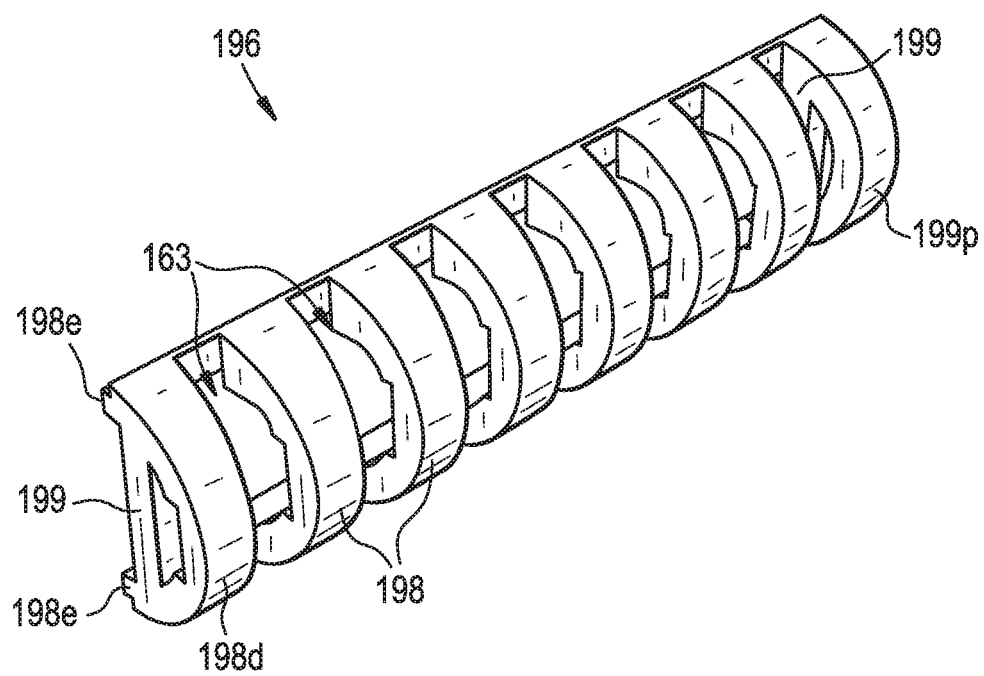
FIG. 8A is an isometric view of a cage member of the outer sleeve of FIG. 6A.
Figure 8B:
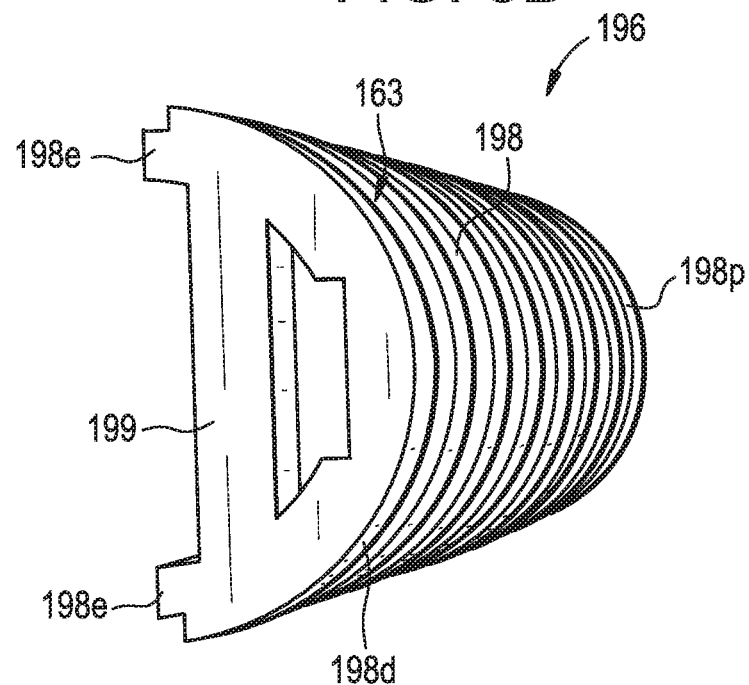
FIG. 8B is a front perspective view of the cage member of FIG. 8A.
Figure 8C:
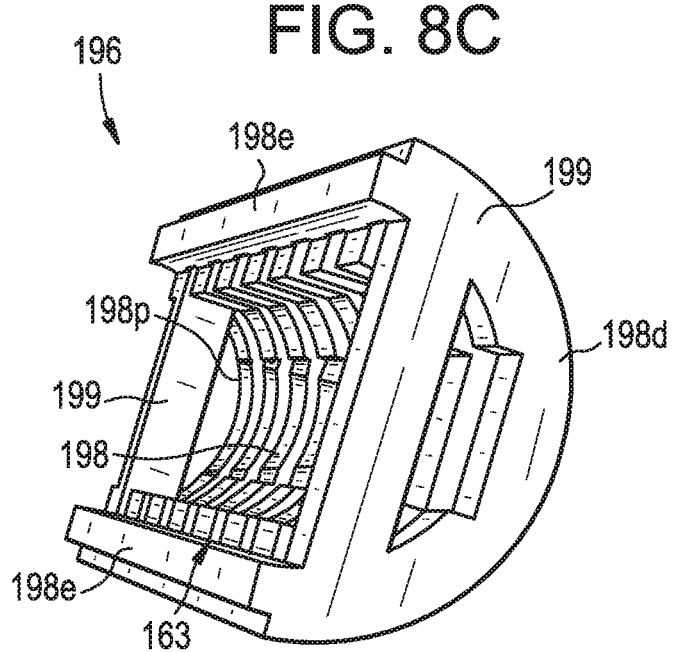
FIG. 8C is a bottom perspective view of the cage member of FIG. 8A.

First and second cage members 196, 197 can be configured to fit on the support arms 159 and within spaces formed between the proximal and distal portions 161p, 161d of the tubular member 161. One embodiment of one of the cage members is illustrated in FIGS. 8A-8C—the cage member 196. As shown, a plurality of radially-extending slots 163 are formed in the cage member 196 along a length of the cage member 196, thus creating a plurality of rows of slots. In the illustrated embodiment, each row includes a single slot, and disposed between the slots 163 are arches 198 having a substantially arcuate outer surface and an inner surface that is configured to be complementary to a surface of an inner guide 164 so they can be mated together. Manufacturing of the cage members 196, 197 can be easy and cost effective because they only require a single cut on each side of the cage member 196, 197 to form.

In the illustrated embodiment, a proximal-most arch 198p and a distal-most arch 198d has a slightly different configuration in that they each includes a retention bar 199 extending radially across the cage member 196 from a first side to a second side. The retention bar 199 can help prevent the inner guide 164 from becoming displaced with respect to the outer sleeve 162, e.g., falling out, in instances in which an ultrasonic weld or other means for coupling the outer sleeve 162 to the inner guide 164 fails. Engagement bars 198e can extend a length of the cage member 196 on a bottom portion thereof, with the engagement bars 198e being configured to engage the support arms 159 when the cage members 196, 197 are coupled to the support arms 159. A method of manufacturing the articulation joint 160 coupled to the end effector 150 is described further below, but generally the cage members 196, 197 can be coupled to one or both of the inner guide 164 and the support arms 159.

A person skilled in the art will recognize that the overall configuration of the tubular member 161 and cage members 196, 197 can vary in many aspects without departing from the spirit of the present disclosure. The materials to make the outer sleeve can be generally stiff, with the slots providing the desired flexibility. In some exemplary embodiments, the tubular member can be made of metal, such as 304 stainless steel, Nitinol, titanium, and carbon-reinforced polymer extrusion, while the cage member can be made of polymers, such as polycarbonate, polyetherimide (e.g., Ultem®), nylon, acrylonitrile butadiene styrene (ABS), or other similar polymers. In instances in which the cage members 196, 197 are ultrasonically welded with the inner guide 164, the materials should be compatible for welding purposes. This is the case for any instance provided for herein in which materials are welded together.

The Second Articulation Joint—Inner Guide

The inner support member or guide 164 of the articulation joint 160 can be of a similar configuration and have similar purposes as described above with respect to the inner support member of guide 60. It likewise results in similar, significant benefits, such as load distribution and allowing components such as the end effector operational components to be fully operational no matter how articulated or straight the end effector is with respect to the elongate shaft.

Figure 6A:
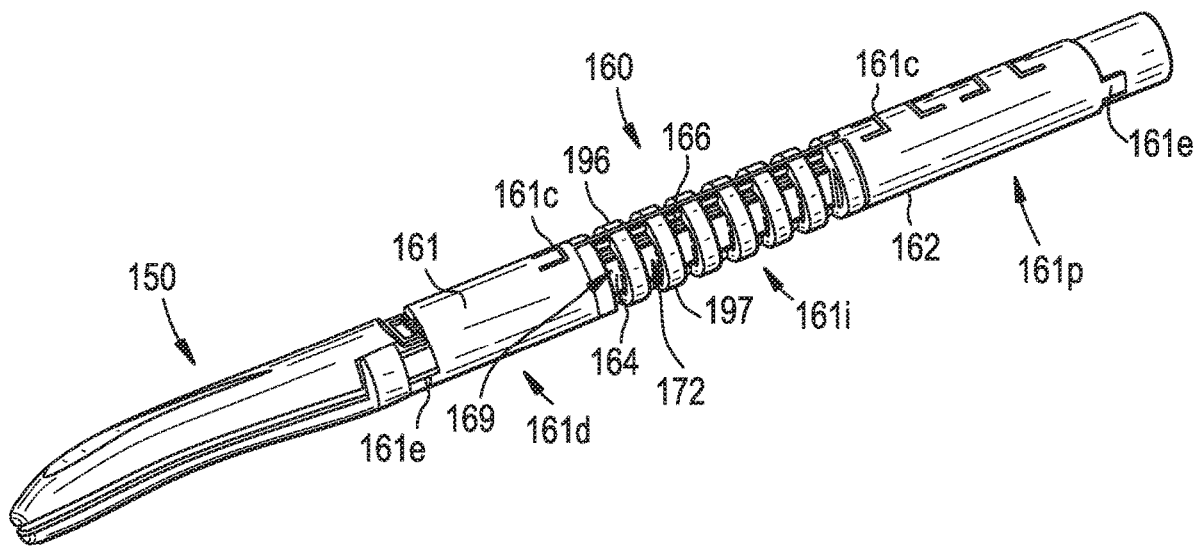
FIG. 6A is an isometric view of another exemplary embodiment of a distal articulation end of a surgical device, the distal articulation end including an end effector and an articulation joint having an outer sleeve and an inner guide, with operational end effector components of the surgical device removed.
Figure 6B:
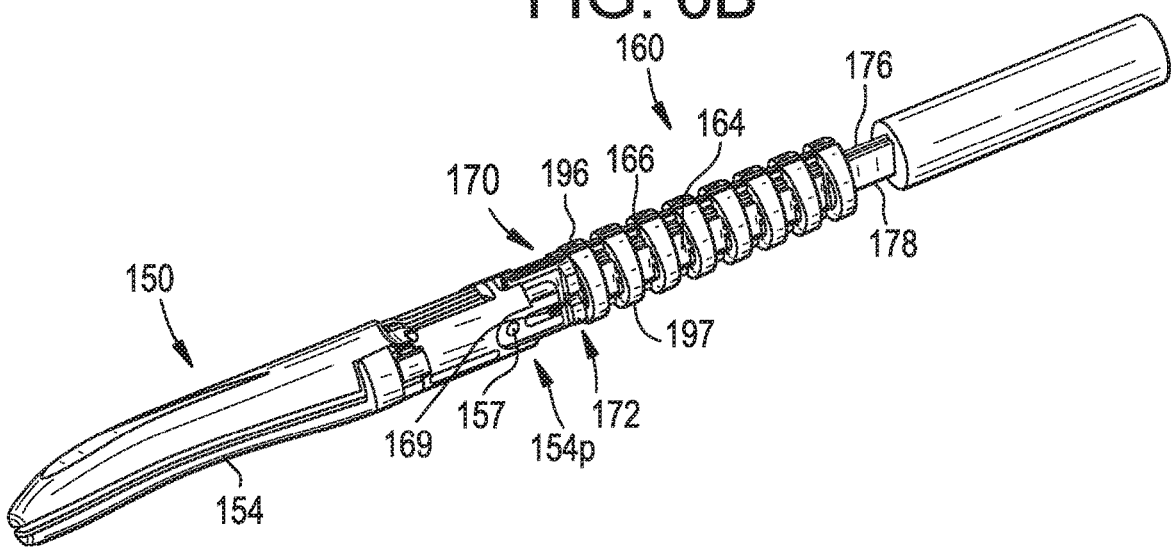
FIG. 6B is an isometric view of the distal articulation end of FIG. 6A with a tubular body of the outer sleeve of the articulation joint removed.

Similar to the inner guide 64, the inner guide 164 can be an elongate body 166 that is made of two complementary bodies 170, 172 that define a central lumen or channel 167 (FIG. 11) to receive a cutting mechanism (not shown) and closure band (not shown), as well as an outer surface 165 (FIG. 9A) that can define portions of a channel 169 through which the articulation bands can extend. One of the complementary bodies, body 170, is illustrated in FIGS. 9A-10B. Unlike the inner guide 64, no portion of the elongate body 166 is substantially cylindrical, although it could be. Instead, the overall configuration of the body 166 is substantially rectangular, and a plurality of ribs 168 are disposed along a length of the outer surface 165. As shown, each rib 168 can include a top wing 168t and a bottom wing 168b that help define the channel 169 that is designed to receive the articulation band. More particularly, each of the first and second wings 168t, 168b includes opposed, facing surfaces 168o that extend substantially perpendicular to the outer surface 165 on which the wings 168t, 168b are disposed. As illustrated in FIGS. 6B and 10B, portions of the wings 168t, 168b, in conjunction with an inner surface of the cage member 196, help define the channel 169 in which the articulation band is received. If the articulation bands were illustrated in FIG. 6B, they could mate to opposed mating protrusions 157 provided for at a proximal portion 154 of a lower jaw 154.

An inner surface 175 of the body 170 can also include a channel 170c extending a length thereof. As shown, the channel 170c can be substantially rectangular in shape such that when the two bodies 170, 172 are mated together, a rectangular channel 167 (FIG. 11) is formed by the opposed first and second inner walls of the first and second bodies 170, 172 that are approximately parallel to each other. The rectangular channel 167 can then receive the cutting mechanism (not shown) and the closure band (not shown).

Figure 9A:
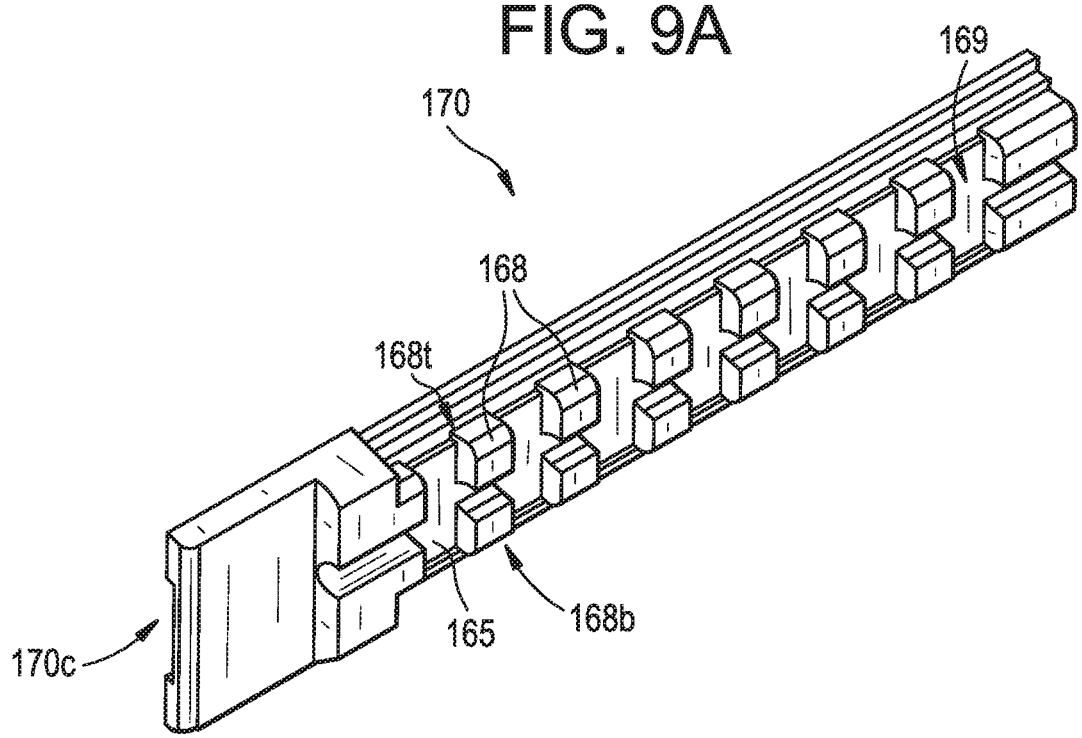
FIG. 9A is a side perspective view of the inner guide of FIG. 6A.
Figure 9B:
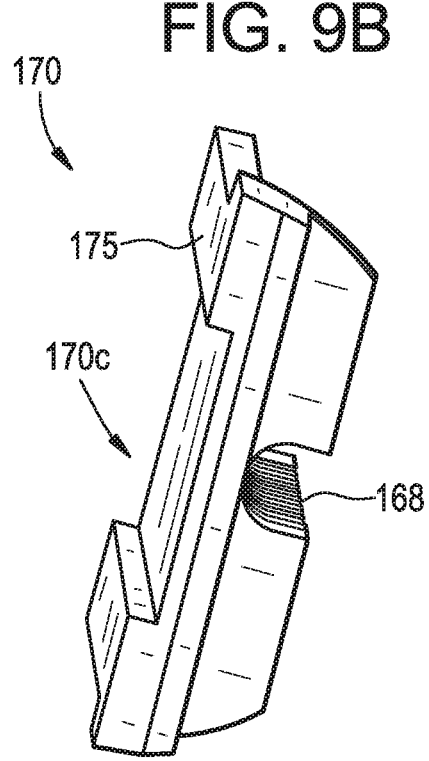
FIG. 9B is a back perspective view of the inner guide of FIG. 9A.
Figure 9C:
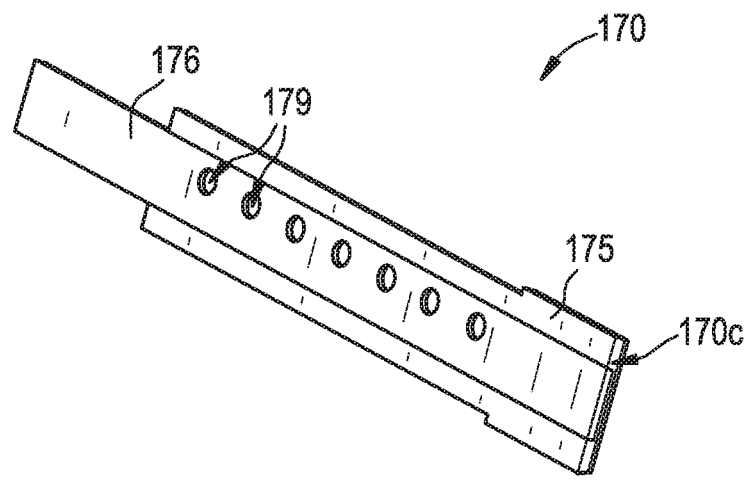
FIG. 9C is a side perspective view of the inner guide of FIG. 9B having a stiffening element coupled thereto.
Figure 10A:
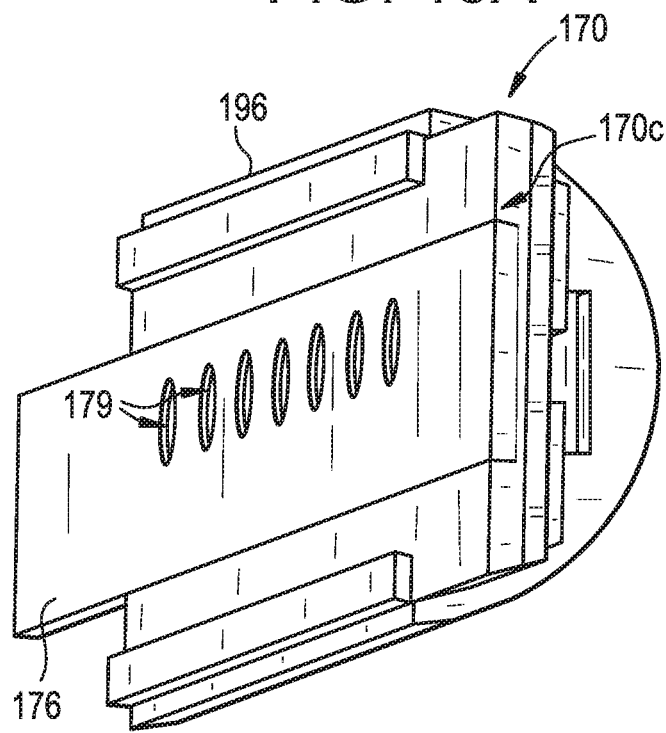
FIG. 10A is a bottom perspective view of the inner guide and the stiffening element of FIG. 9C with the inner guide coupled to the cage member of FIG. 8A.
Figure 10B:
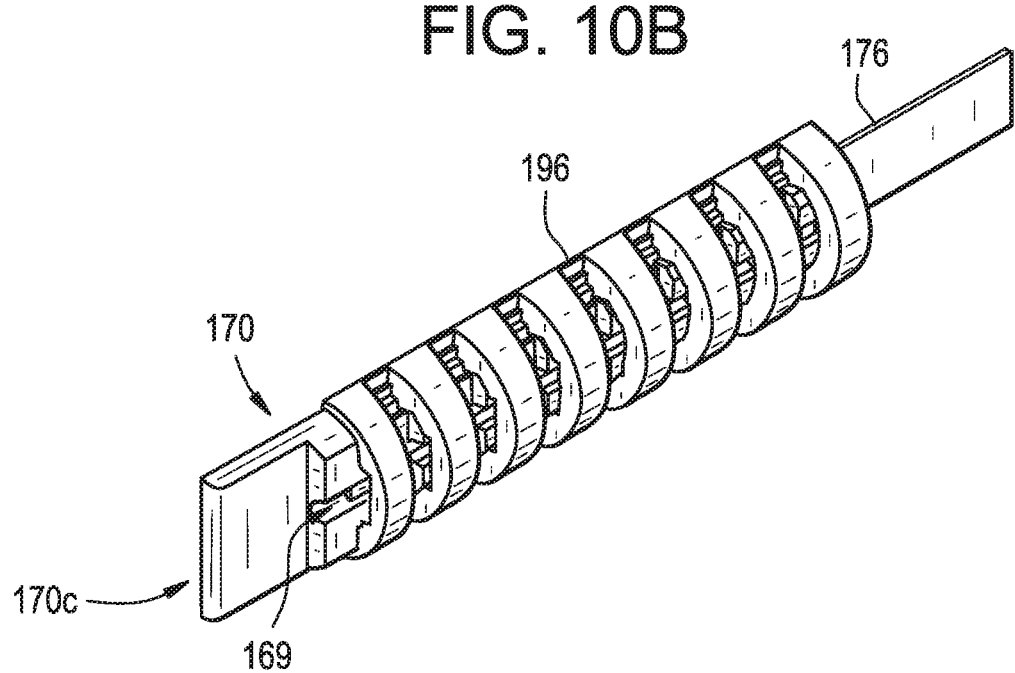
FIG. 10B is a side perspective view of the inner guide, stiffening element, and cage member of FIG. 10A.

As shown in FIGS. 9C and 10A, the channel 170c can also be configured to receive a stiffening element 176. The stiffening element 176 can mate with the inner guide body 170 using techniques similar to those described above with respect to the stiffening elements 76, 78 and inner guide 64, and thus the stiffening element 176 can include a plurality of lumens 179 formed therein to assist in the mating. A complementary stiffening element 178 (FIG. 6B) can also be provided. In the illustrated embodiment, the stiffening elements 176, 178 can extend proximally from the inner guide 164, towards an elongate outer shaft 140 (FIG. 11), which can help during manufacturing and/or to couple the stiffening elements 176, 178, and thus the inner guide 164, to the elongate outer shaft. Alternatively, or additionally, the stiffening elements 176, 178 can extend distally beyond the inner guide 164 for similar reasons. Further, as shown in FIG. 10A, the inner guide 164 can be coupled to the cage member 196, for instance by causing the cage member 196 to be snap fit onto the inner guide 164 or ultrasonically welding some portion of them together. Alternatively, they may be more loosely coupled together, for instance by sliding the inner guide 164 into the illustrated location with respect to the cage member 196, with the additional components of the device helping to hold them in place and/or welding the cage member 196 to the inner guide 164 at one or more locations. As illustrated, the outer sleeve 162 is disposed radially outward from the inner guide 164, or in the alternative, the inner guide 164 is disposed radially inward from the outer sleeve 162.

Figure 11:
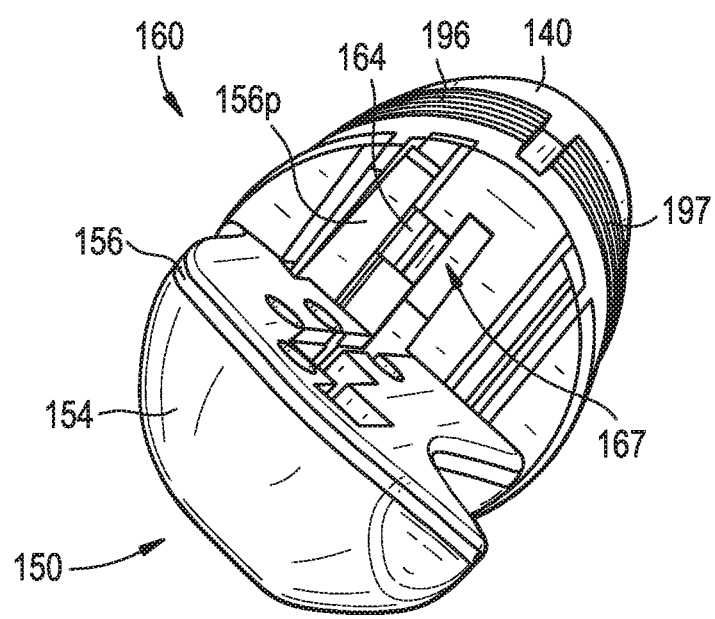
FIG. 11 is a front perspective view of the distal articulation end of FIG. 6A with a top jaw of the end effector removed.

FIG. 11 illustrates the articulation joint 160 assembled with an elongate outer shaft 140 and an end effector 150 having jaws 152, 154, but with a top jaw 152 removed. As with the other figures describing this embodiment, none of the end effector operational components are illustrated, but they can be disposed as described in other embodiments provided for herein or as otherwise known to those skilled in the art in view of the present disclosure. As shown, the central lumen 167 can extend through the articulation joint 160. Further, this embodiment illustrates that the lower jaw 154 can include an electrode 156, which can be powered by a wire connected to a proximal portion 156p of the electrode 156 disposed in the jaw 154.

A Third Articulation Joint

Figure 12A:
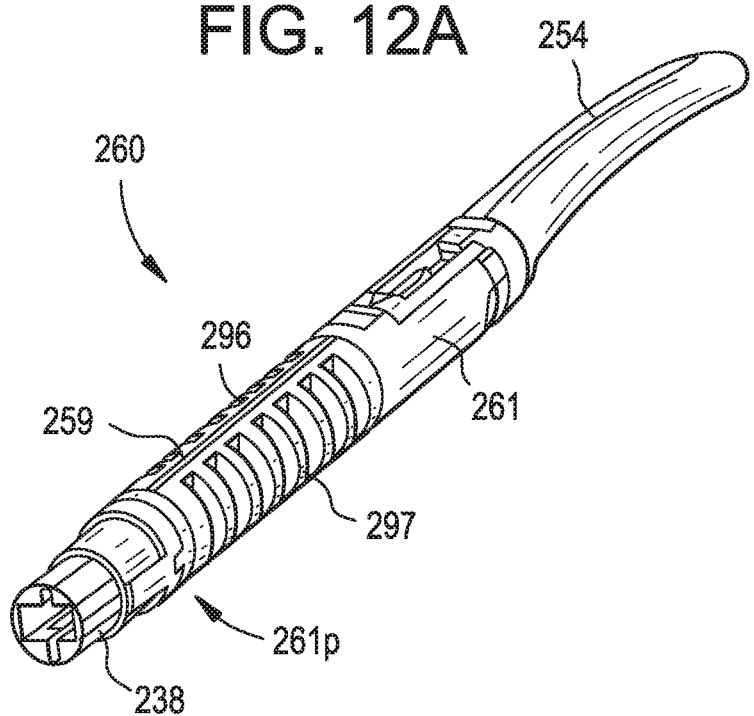
FIG. 12A is an isometric view of still another exemplary embodiment of a distal articulation end of a surgical device, the distal articulation end including an end effector and an articulation joint having an outer sleeve and an inner guide, with operational end effector components of the surgical device removed.
Figure 12B:
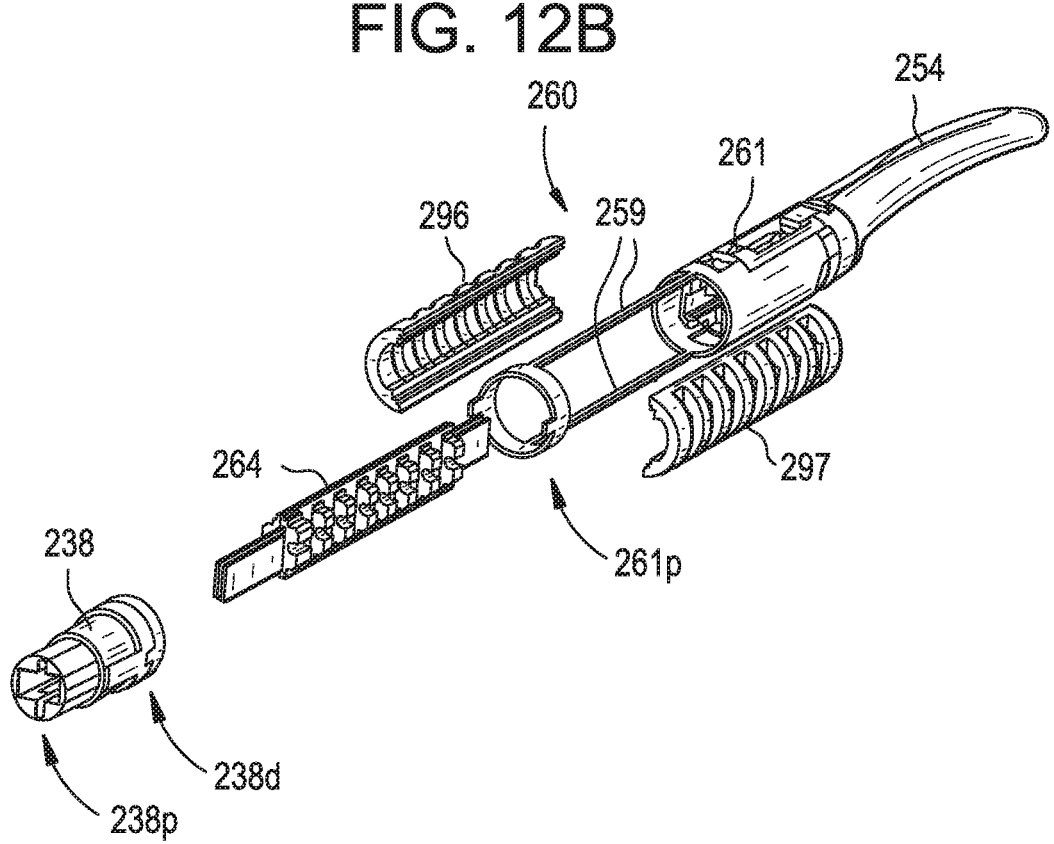
FIG. 12B is an exploded view of the distal articulation end of FIG. 12A.

FIGS. 12A and 12B illustrate a third exemplary articulation joint 260 having a very similar configuration as the second articulation joint 160, and is primarily provided to both illustrate an electrically insulative adapter 238 and to be referenced in a method of manufacturing an articulation joint, as shown in FIGS. 13A-13H.

As shown, the articulation joint 260 can include an outer sleeve that includes a tubular member 261 and cage members 296, 297 disposed on opposite sides of opposed support arms 259 of the tubular member 261, an inner guide 264 having opposed stiffening elements 276, 278 disposed therein, a lower jaw 254 coupled to the tubular member 261 and configured to be articulated by articulation bands (not shown) disposed through the articulation joint 260, and an electrically insulative adapter 238 coupled to a proximal end 261p of the tubular member 261. The electrically insulative adapter 238 can have a distal end 238d that is complementary to the proximal end 261p of the tubular member 261 so they can be easily coupled together, and likewise a proximal end 238 p that is complementary to a distal end of an outer elongate shaft of a surgical device with which the third articulation joint 260 is used. The electrically insulative adapter 238 can help electrically isolate the outer elongate shaft, as well as other components proximal of the articulation joint 260 that are also conductive, from conductive components that are disposed distal of the adapter 238, such as the tubular member 261, and/or the jaws.

Manufacturing the Third Articulation Joint

Figure 13A:
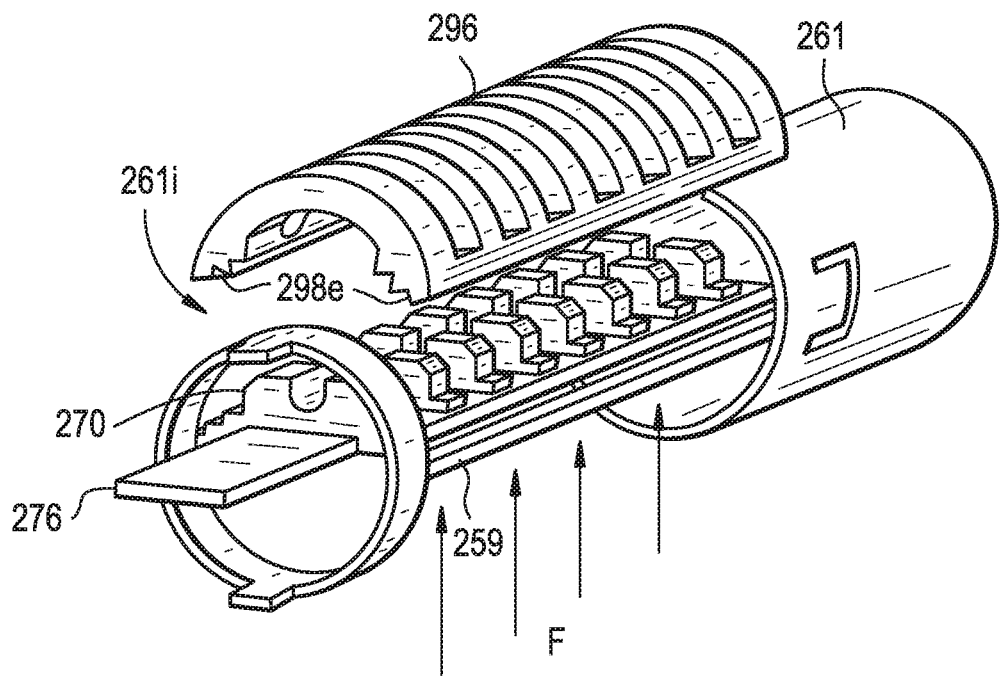
FIG. 13A-13H schematically illustrate one exemplary embodiment for manufacturing the distal articulation end of FIG. 12A.
Figure 13B:
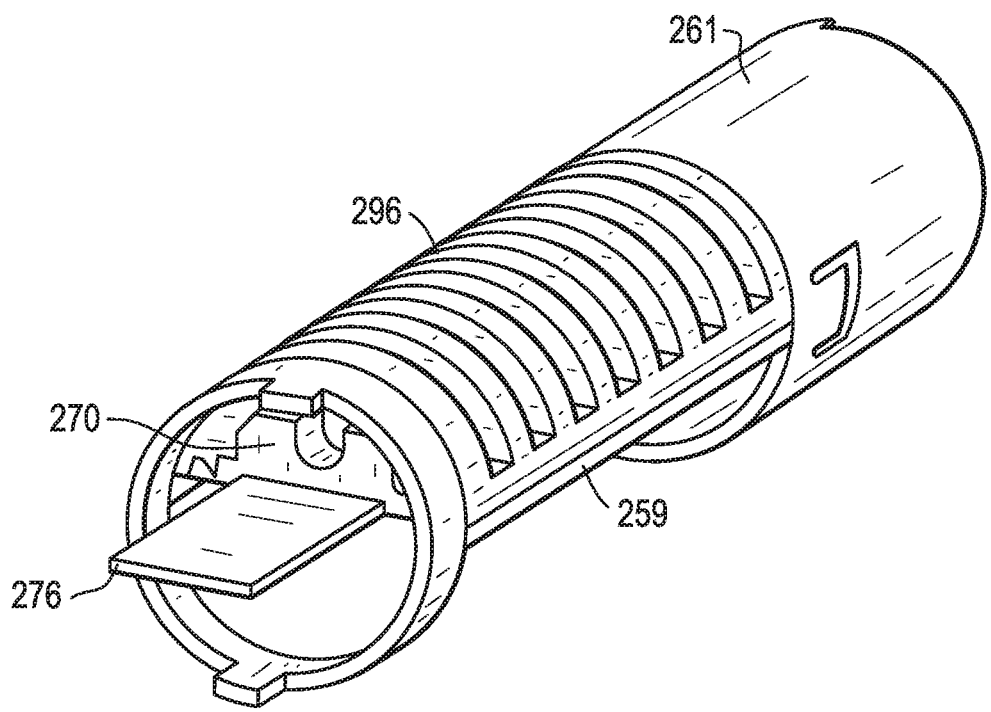
Figure 13C:
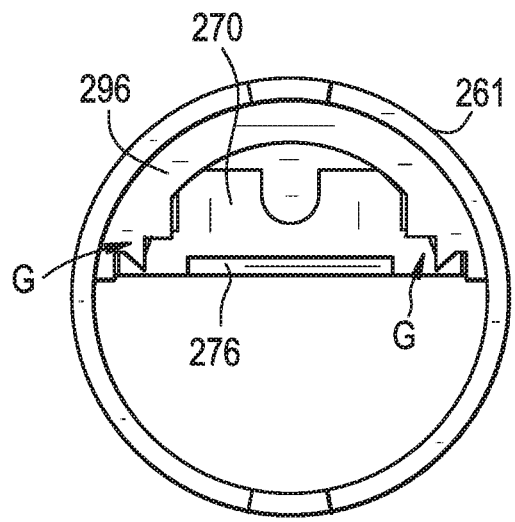

FIG. 13A illustrates the tubular member 261 having one body 270 of the inner guide 264 coupled thereto. Either or both the inner guide body 270 and a stiffening element 276 associated therewith can be coupled to a receiving feature associated with the tubular member 261. Any techniques known for coupling one component to another can be used, and in the illustrated embodiment one of the stiffening element 276 and a distal end of the inner guide body 270 is interference fit with a receiving feature of the tubular member 261. Either before or after the inner guide body 270 is coupled to the tubular member 261, one of the cage members 296 can be passed into an intermediate section 261i of the tubular member 261 and engagement bars 298e of the cage member 296 can contact the support arms 259 such that the support arms exert a force in a direction F onto the cage member 296 to hold it in place. The cage member 296 can be coupled to the support arms 259 and/or the inner guide body 270, for example, by ultrasonically welding the cage member 296 to the inner guide body 270 at locations G at the proximal end, illustrated in FIG. 13C. As shown in FIG. 13B, the result is that the outer surface of the cage member 296 is substantially flush with the tubular member 261.

Figure 13D:
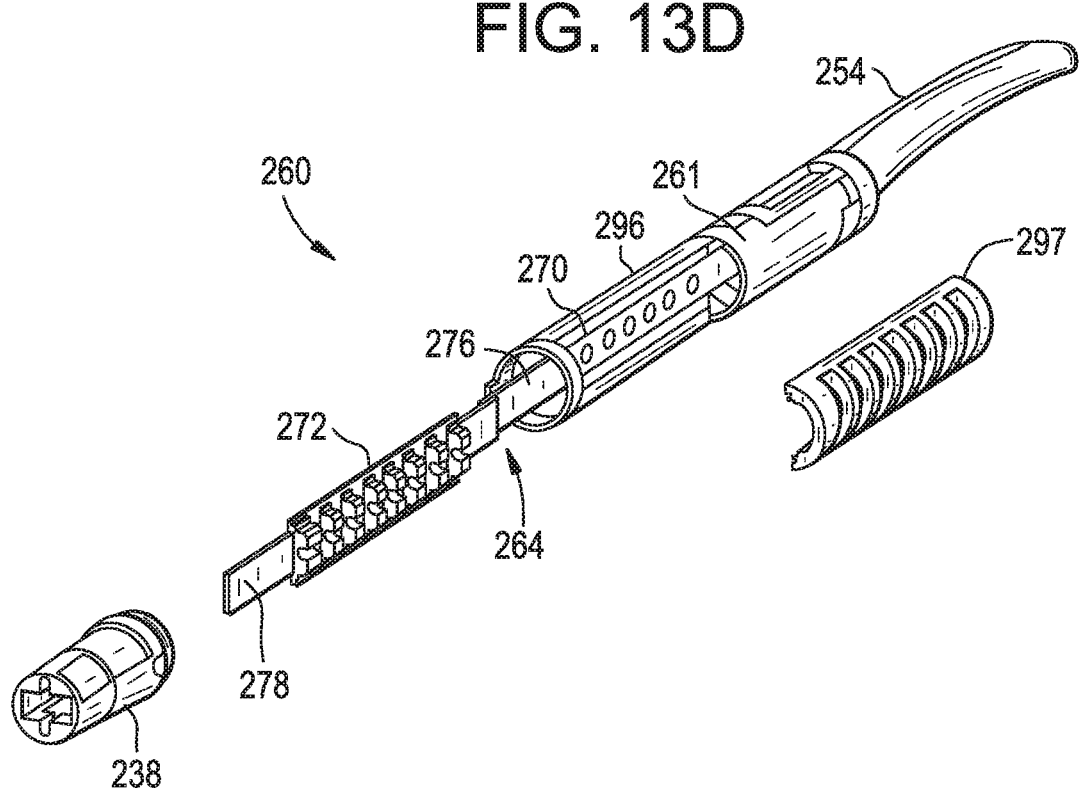
Figure 13E:
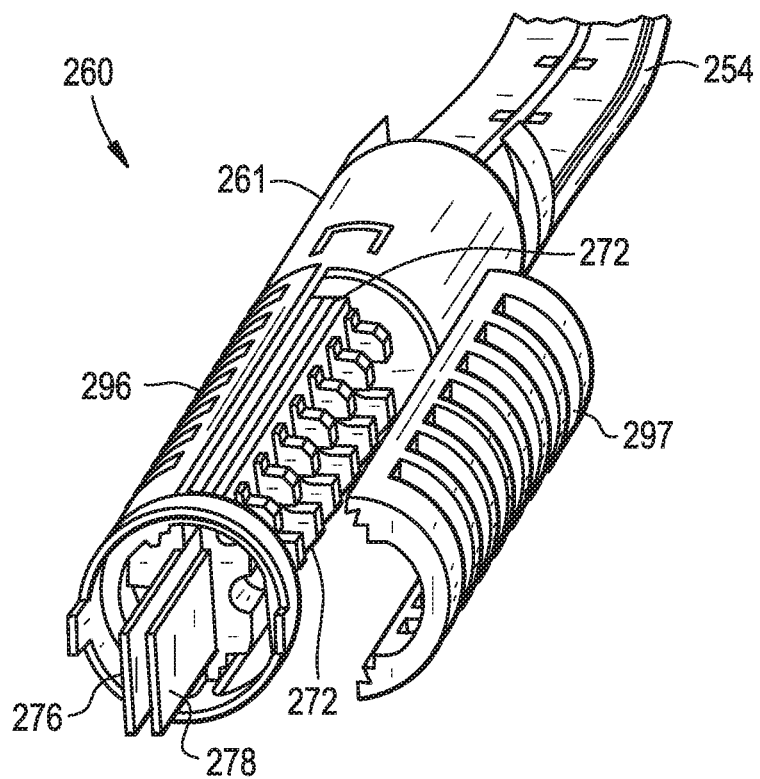
Figure 13F:
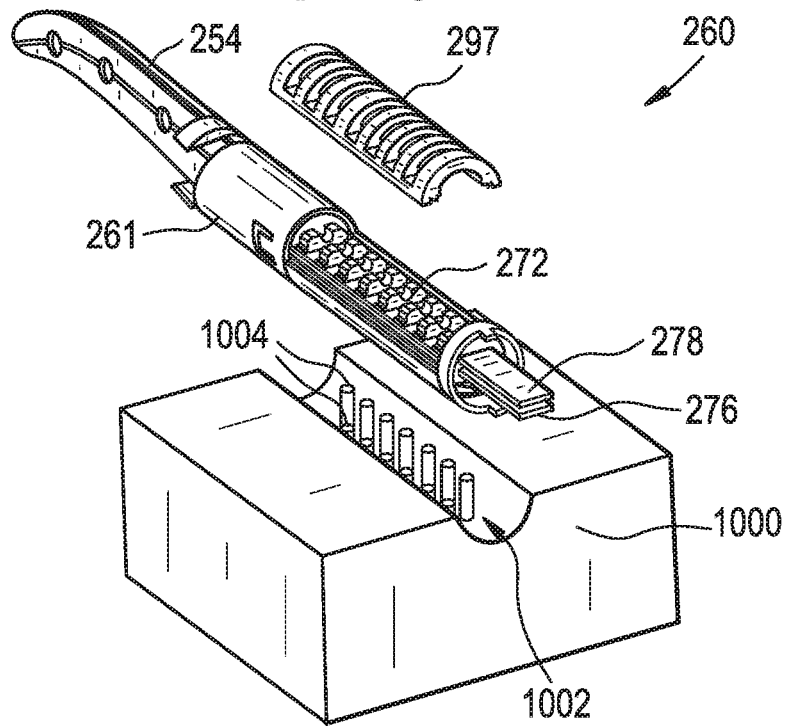
Figure 13G:
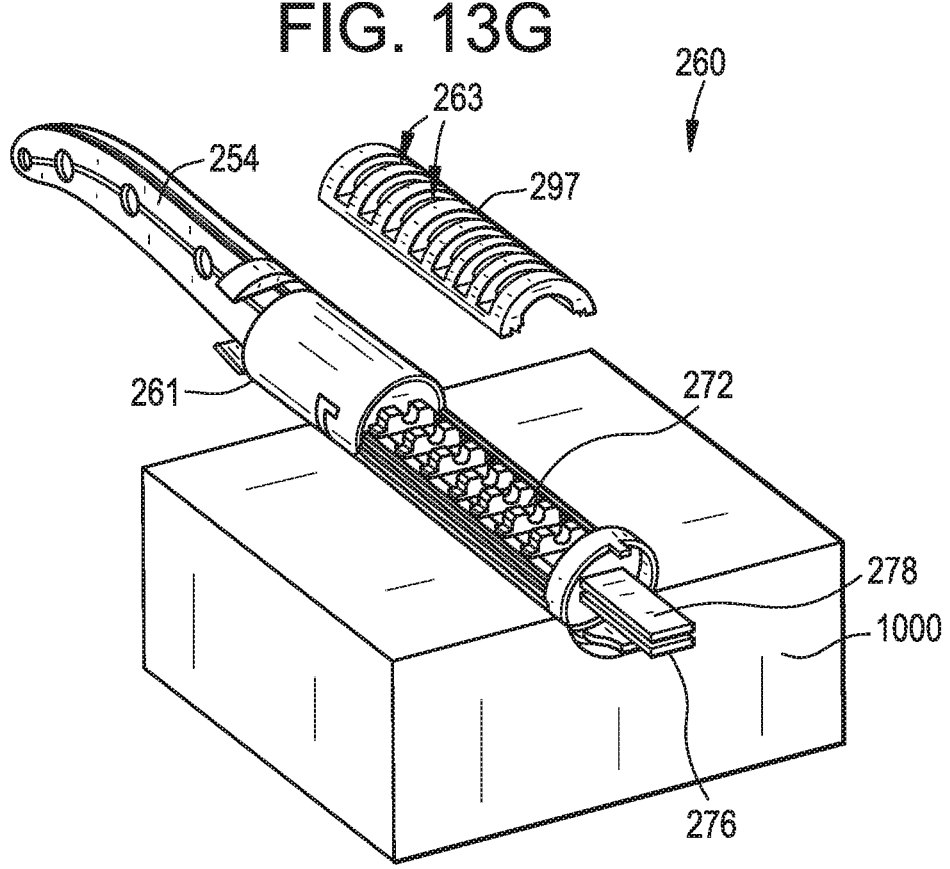
Figure 13H:
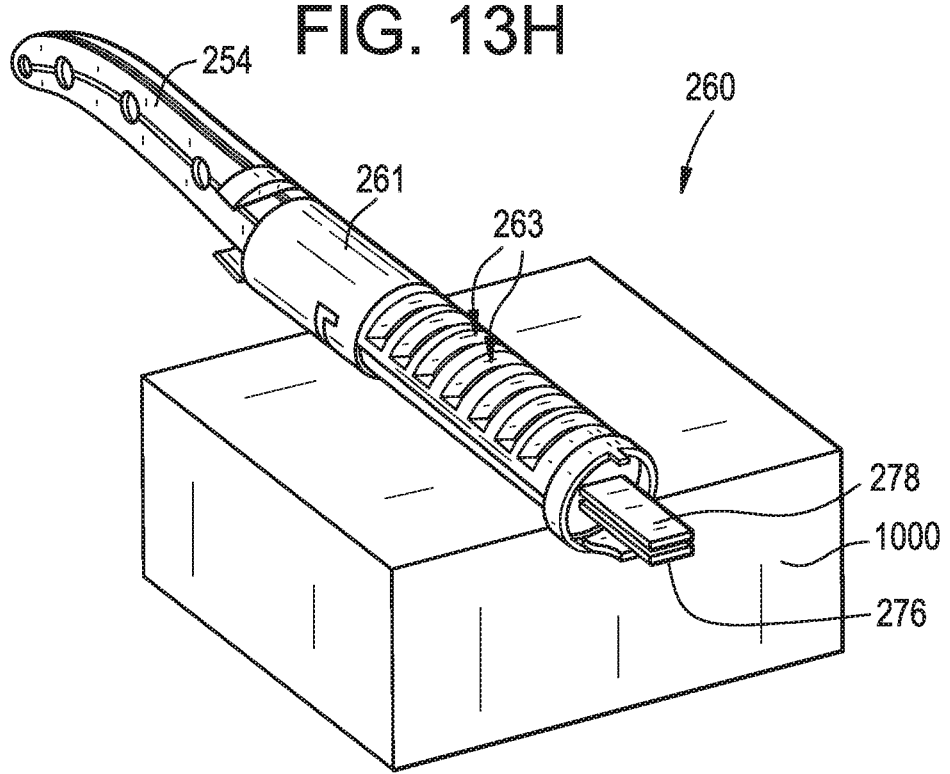

FIG. 13D illustrates that a lower jaw 254 of an end effector 250 is coupled to the tubular member 261. Any techniques known for coupling one component to another can be used, and in the illustrated embodiment opposed pins are used to couple the lower jaw 254 to the tubular member 261. Notably, the lower jaw 254 can be coupled to the tubular member 261, and the articulation joint 260 more generally, at any time, including before any other portion of the inner guide 264 and the cage members 296, 297 are associated with the tubular member 261 or after the entire articulation joint 260 is assembled. As shown in FIGS. 13D and 13E, the other body 272 of the inner guide 264, and its associated stiffening element 278, as well as the other cage member 297, can be coupled to the tubular member 261 and to each other in a similar fashion as described above with respect to the first body 270 of the inner guide 264 and the first cage member 296. Further, as shown in FIGS. 13F-13H, a mounting block 1000 can be used to assist in coupling the cage member 297 to the tubular member 261 and/or the inner guide 264. The mounting block 1000 can include a channel 1002 that is sized and shaped to receive the tubular member 261, and optionally, can include one or more pegs 1004 extending upwards from a surface of the channel 1002 to assist in receiving and holding the articulation joint 260 in place during manufacturing. In particular, the pegs 1004 can be sized and spaced to sit in slots 263 of the cage member 260. A person skilled in the art will recognize many other configurations are possible for helping to maintain a location of the articulation joint 260 with respect to the mounting block 1000 during manufacturing.

Further, the described manufacturing method with respect to FIGS. 13A-13H is by no means limiting. A person skilled in the art in view of the present disclosure would understand how to manufacture any of the surgical devices and/or articulation joints provided for herein or otherwise derivable from the present disclosure. The techniques described with respect to FIGS. 13A-13H can be applied to other configurations and/or adapted for use in manufacturing other variations of the surgical devices. Likewise, one or more aspects of the described method can be changed, including having steps modified, added, or removed, while manufacturing the device without departing from the spirit of the present disclosure.

A Fourth Articulation Joint

Figure 14:
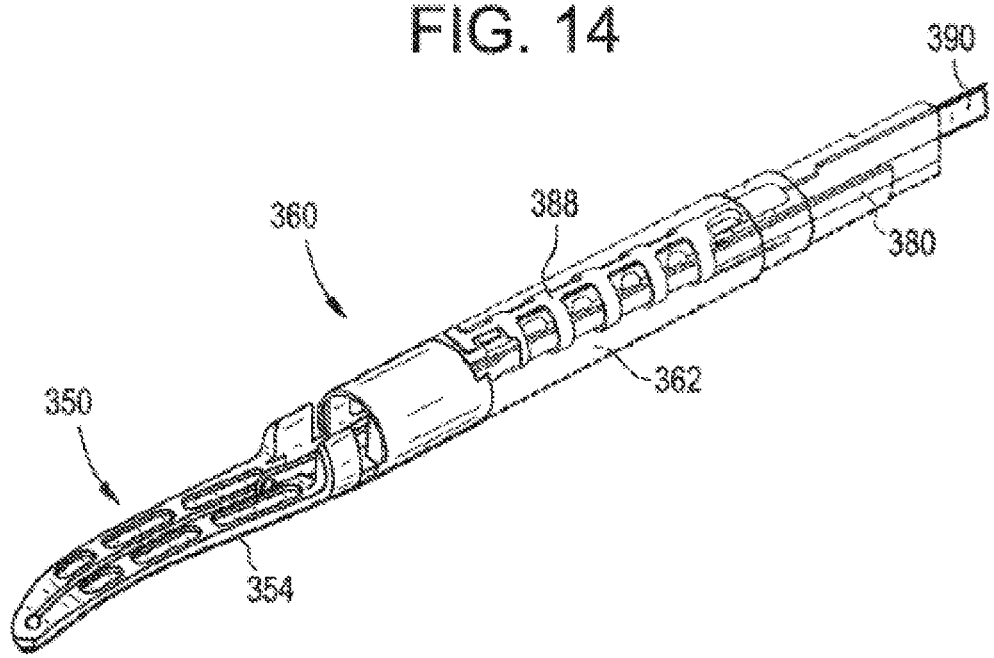
FIG. 14 is an isometric view of another exemplary embodiment of a distal articulation end of a surgical device, the distal articulation end including an end effector and an articulation joint having an outer sleeve, an inner guide, and an intermediate sleeve, with the outer sleeve in phantom.

Another exemplary embodiment of an articulation joint 360 is illustrated in FIGS. 14-17. FIG. 14 shows a distal end of a surgical device with a top jaw removed and an outer sleeve 362 of the articulation joint 360 in phantom so that an intermediate sleeve or stabilization spine 388 of the articulation joint 360 can be better illustrated. The outer sleeve 362 in phantom can be generally tubular in nature and can be configured to couple to a proximal end of an end effector 350.

Figure 16:
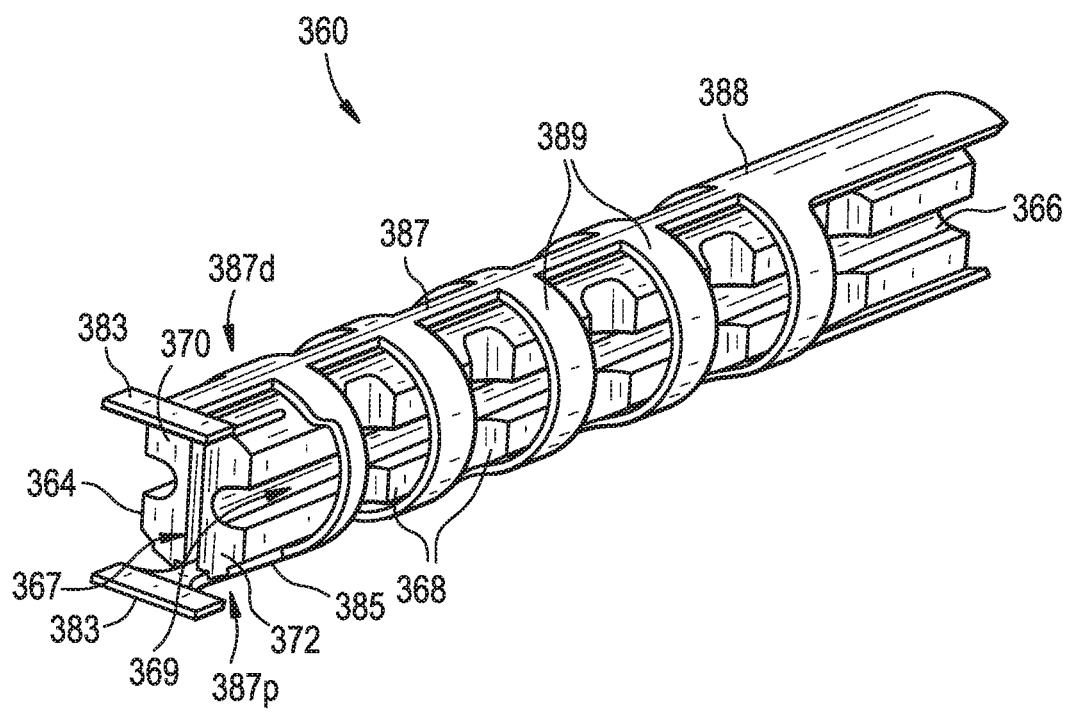
FIG. 16 is an isometric view of the inner guide and the intermediate sleeve of the articulation joint of FIG. 14.

In the illustrated embodiment, it is the intermediate sleeve 388 that couples to an inner guide 364 of the articulation joint 360 to provide stability and flexibility for the articulation joint 360 generally, and channels 369 for receiving articulation bands 380, 382. The inner guide 364 can be formed in manners similar to those described herein, and thus, as shown in FIG. 16, it is an elongate body 366 that is made of two similarly sized and shaped bodies 370, 372 that are coupled together with ribs 368 disposed on outer surfaces 365 of each of the bodies 370, 372 such that the ribs 368 are disposed substantially on opposite sides of the elongate body 366 from one another. Further, an inner channel 367 can be formed by the two bodies 370, 372 so that a cutting mechanism 390 and/or a closure band 384 can be passed therethrough. Stiffening elements can be associated with the inner channel 367 as described in other embodiments, although they are not illustrated in the present embodiment. As with all embodiments, the stiffening elements can be beneficial, but are not required.

Figure 15:
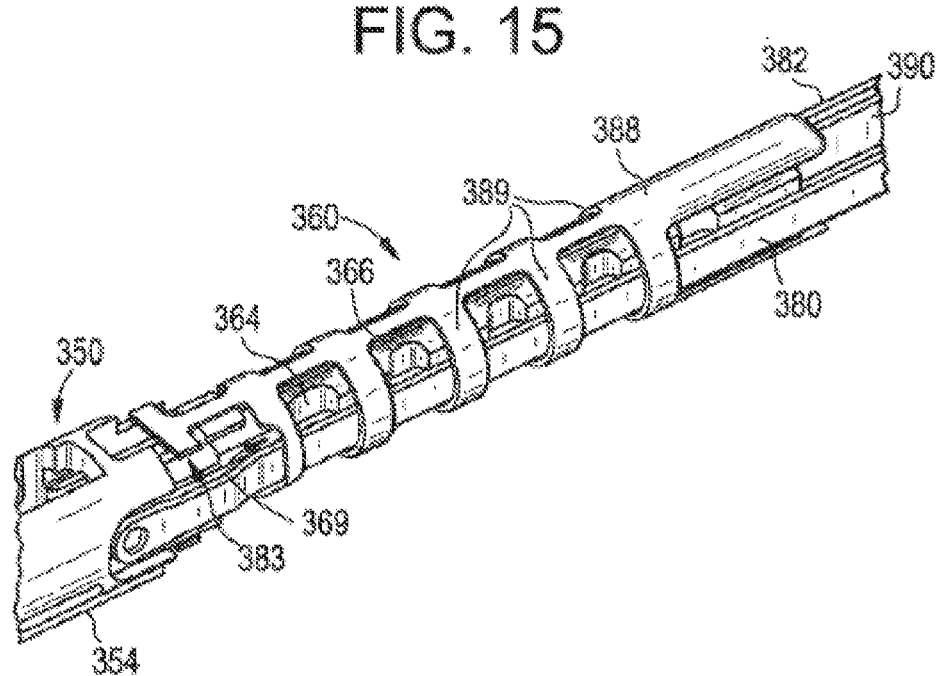
FIG. 15 is a detailed isometric view of the distal articulation end of FIG. 13 with the outer sleeve hidden from view.

As shown in FIG. 15, the intermediate sleeve 388 can include a top longitudinal spine 387 extending from a proximal end 388p of the sleeve 388 to a distal end 388d of the sleeve 388. A plurality of rings 389 can extend from the top spine 387 along a length thereof. In the illustrated embodiment there are five rings 389, although any number can be used. The rings 389 can be similarly shaped, or some can have different surfaces. For example, in the illustrated embodiment, a distal-most ring 389d has a thickness that is less than a thickness of the other rings so that it better interacts with a different sized distal-most rib of the inner guide 364. The rings 389 can extend radially towards a bottom longitudinal spine 385 that is approximately parallel to the top spine 387 and connect thereto. The bottom spine 385 can have a similar formation as the top spine 387, and the rings 389 can be coupled thereto. In alternative embodiments, there may be no bottom spline and the rings can fully encircle the inner guide, or alternatively, the rings may not be full rings and instead may include first and second wings that may just wrap around a portion of the inner guide before terminating prior to connecting on the underside of the inner guide. The intermediate sleeve 388 can help hold the bodies 370, 372 together, and additionally, can prevent the articulation bands 380, 382 from buckling, as well as prevent an end effector 350 from becoming displaced with respect to an elongate shaft coupled to the other end of the articulation joint 360. In some embodiments, the outer sleeve 362 can be made of polymers, such as polycarbonate, polyetherimide (e.g., Ultem®), nylon, acrylonitrile butadiene styrene (ABS), or other similar polymers, and the intermediate sleeve 388 can be made of metals, such as 304 stainless steel, Nitinol, titanium, and other metals having a substantially higher modulus of elasticity in comparison to the polymers used for forming the outer sleeve 362.

Figure 17:
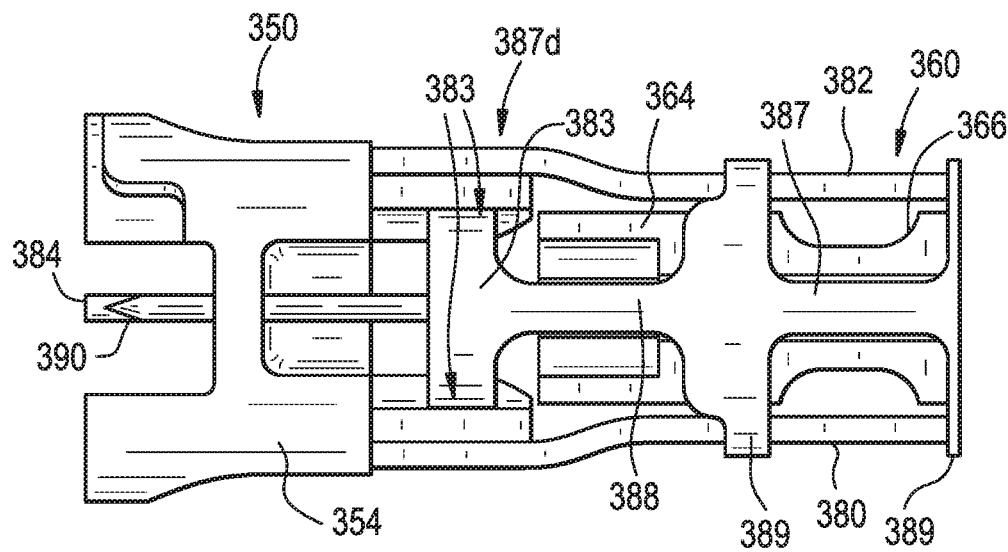
FIG. 17 is a detailed top view of the intermediate sleeve coupled to the end effector of FIG. 14.

As also shown in FIG. 15, the ribs 368 of the inner guide 364 and the rings 389 of the intermediate sleeve 388 can form a channel 369 through which the articulation band 380 can be passed. A similar channel can be disposed on the opposed side for the other articulation band 382. The articulation bands 380, 382 can be mated to a lower jaw 354 of the end effector 350, as shown in FIG. 17, using the techniques provided for herein or otherwise known to those skilled in the art.

In some embodiments, a distal end 387d, 385d of the top and bottom spines 387, 385 can each include a tab 383 that extends approximately perpendicular to the respective spines 387, 385. As shown in FIGS. 15 and 17, the tabs 383 can be used to mate the articulation joint 360 to the end effector 350. More specifically, in the illustrated embodiment the tabs 383 are laser welded to proximal extensions 354e of the lower jaw 354, although other techniques for coupling the articulation joint 360 to the end effector 350 and/or coupling the tabs 383 to another portion of the end effector 350 is also possible. By mating the sleeve 388 to the lower jaw 354, a load path produced, for example, by an upper jaw clamping down onto the lower jaw 354, can be better distributed to the articulation joint 360. A proximal end of the sleeve 388 can be mated to an adjacent part of the device as well, for example an outer elongate shaft.

A Fifth Articulation Joint

Figure 18:
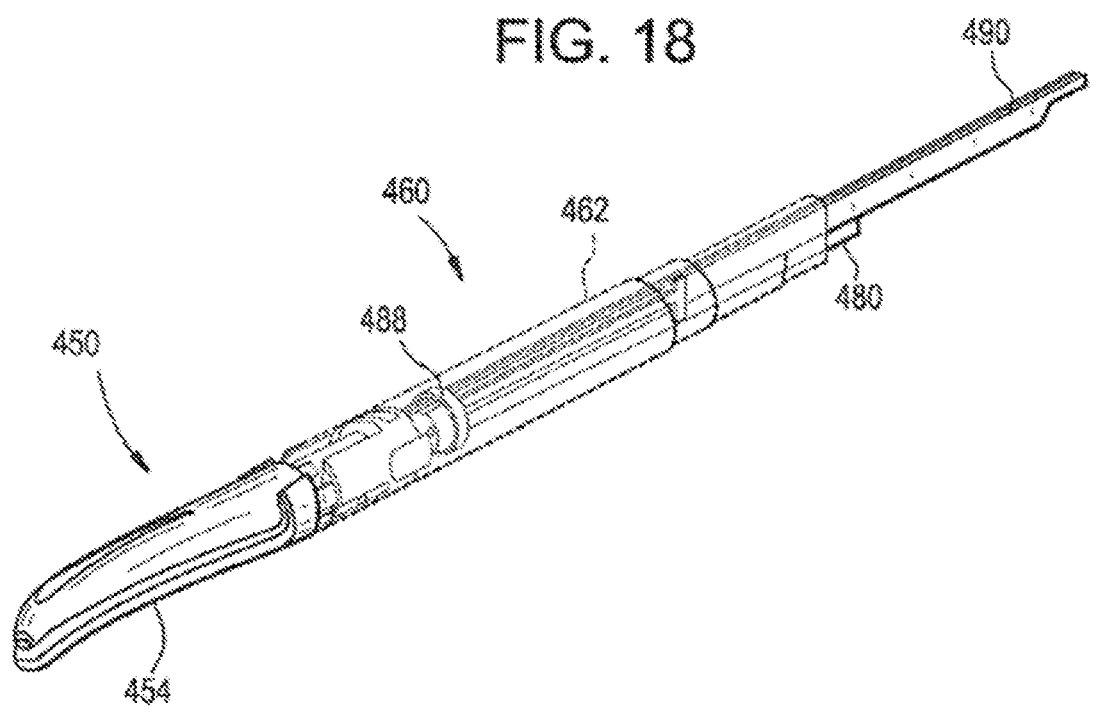
FIG. 18 is an isometric view of yet another exemplary embodiment of a distal articulation end of a surgical device, the distal articulation end including an end effector and an articulation joint having an outer sleeve, an inner guide, and an intermediate ring, with the outer sleeve in phantom.

Yet another exemplary embodiment of an articulation joint 460 is illustrated in FIGS. 18-21. FIG. 18 shows a distal end of a surgical device with an outer sleeve 462 of the articulation joint 460 in phantom so that the inner guide and intermediate or stabilization ring 488 of the articulation joint 460 can be better illustrated. The outer sleeve 462 in phantom can be formed in a manner similar to the sleeve 362.

Figure 19:
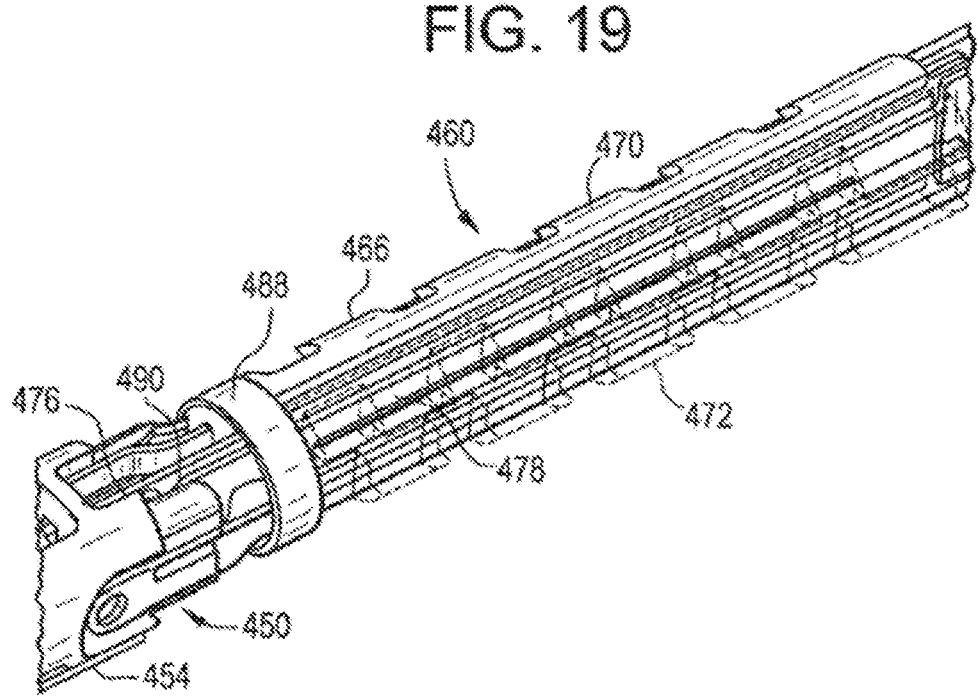
FIG. 19 is a detailed isometric view of the distal articulation end of FIG. 18 with the outer sleeve hidden from view and a portion of the inner guide in phantom.
Figure 20:
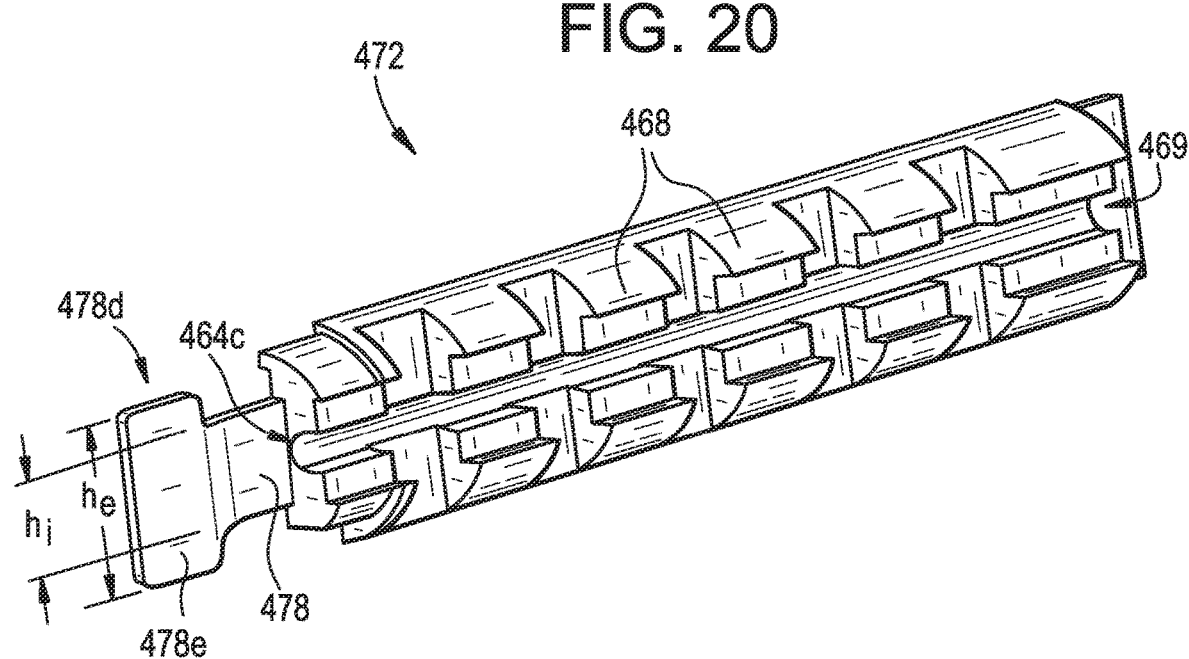
FIG. 20 is an isometric view of one body of the inner guide of FIG. 18.

In the illustrated embodiment, the intermediate ring 488, in conjunction with the inner guide, provides stability and flexibility for the articulation joint 460 generally, and channels 469 for receiving articulation bands 480, 482. The inner guide can be formed in manners similar to those described herein, and thus, as shown in FIGS. 19 and 20, it is an elongate body 466 that is made of two similarly sized and shaped bodies 470, 472, the latter of which is shown in FIG. 20. The bodies 470, 472 are coupled together with ribs 468 disposed on outer surfaces of each of the bodies 470, 472 such that the ribs 468 are disposed substantially on opposite sides of the elongate body 466 from one another. As shown best in FIG. 20, the ribs 468 can define a channel 469 in which the articulation band 480 can be received, and as shown best in FIG. 21, the articulation bands 480, 482 can be disposed between the inner guide and the intermediate ring 488. Further, turning back to FIG. 20, a more central channel 464c can be formed in the body 472, for instance to receive a wire to power an electrode of the end effector. The intermediate ring 488 can help hold the bodies 470, 472 together, and additionally, can prevent distal ends of the articulation bands 480, 482 from buckling, as well as prevent an end effector 450 from becoming displaced with respect to an elongate shaft coupled to the other end of the articulation joint 460. In some embodiments, the outer sleeve 462 can be made of polymers, such as polycarbonate, polyetherimide (e.g., Ultem®), nylon, acrylonitrile butadiene styrene (ABS), or other similar polymers, and the intermediate sleeve 488 can be made of metals, such as 304 stainless steel, Nitinol, titanium, and other metals having a substantially higher modulus of elasticity in comparison to the polymers used for forming the outer sleeve 362.

Figure 21:
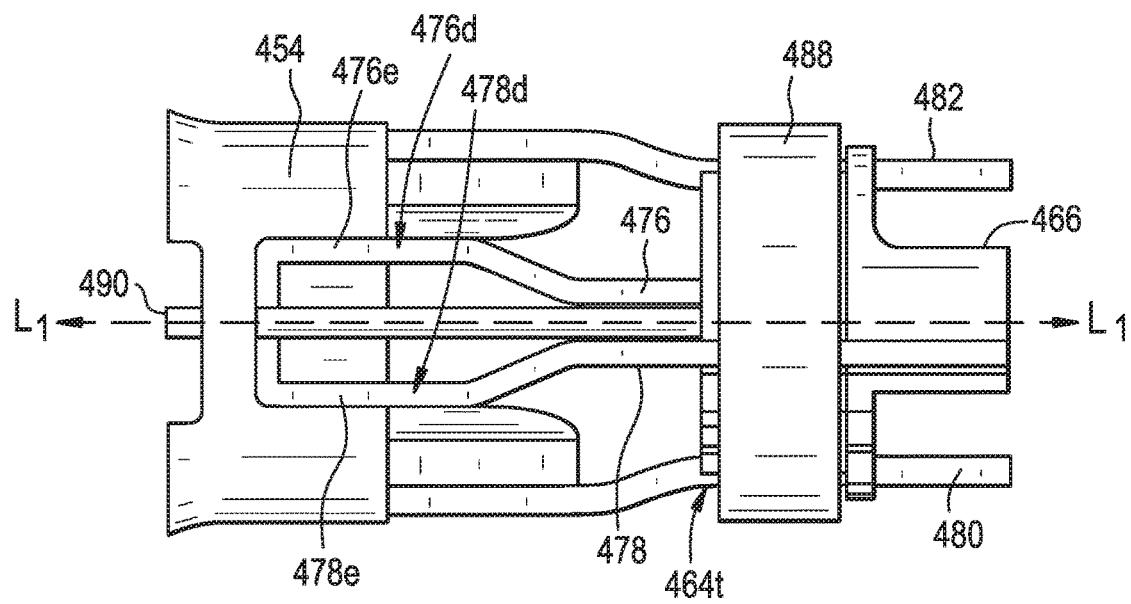
FIG. 21 is a detailed top view of the intermediate ring and the inner guide of FIG. 18, the inner guide being coupled to the end effector.

An inner channel 467 (not visible) can be formed by the two bodies 470, 472 so that a cutting mechanism 490 and/or a closure band (not shown) can be passed therethrough. Further, as shown, stiffening elements 476, 478 can be associated with the inner channel 467 using techniques described elsewhere herein or otherwise known to those skilled in the art. As shown in FIGS. 20 and 21, distal ends 476d, 478d of the stiffening elements 476, 478 can include extensions 476e, 478e that are configured to mate to a lower jaw 454 of the end effector 450, for example, by ultrasonically welding them to the jaw 454. By mating the stiffening elements 476, 478 to the lower jaw 454, a load path produced, for example, by an upper jaw clamping down onto the lower jaw 454, can be better distributed to the articulation joint 460. Alternatively, the extensions 476 e, 478 e can extend distally beyond a terminal end 464t of the inner guide but not mate to the lower jaw 454, for instance when another portion of the inner guide is coupled to the end effector. In the illustrated embodiment, a height he of the extensions 476e, 478e is greater than a height h1 of an intermediate portion of the stiffening elements 476, 478. Additionally, as shown in FIG. 21, the extensions 476e, 478e can extend radially outward from a central longitudinal axis L1 of the inner guide such that the extensions 476e, 478e are further away from the central longitudinal axis L1 than the intermediate portions of the stiffening elements 476, 478.

A Sixth Articulation Joint

Figure 22:
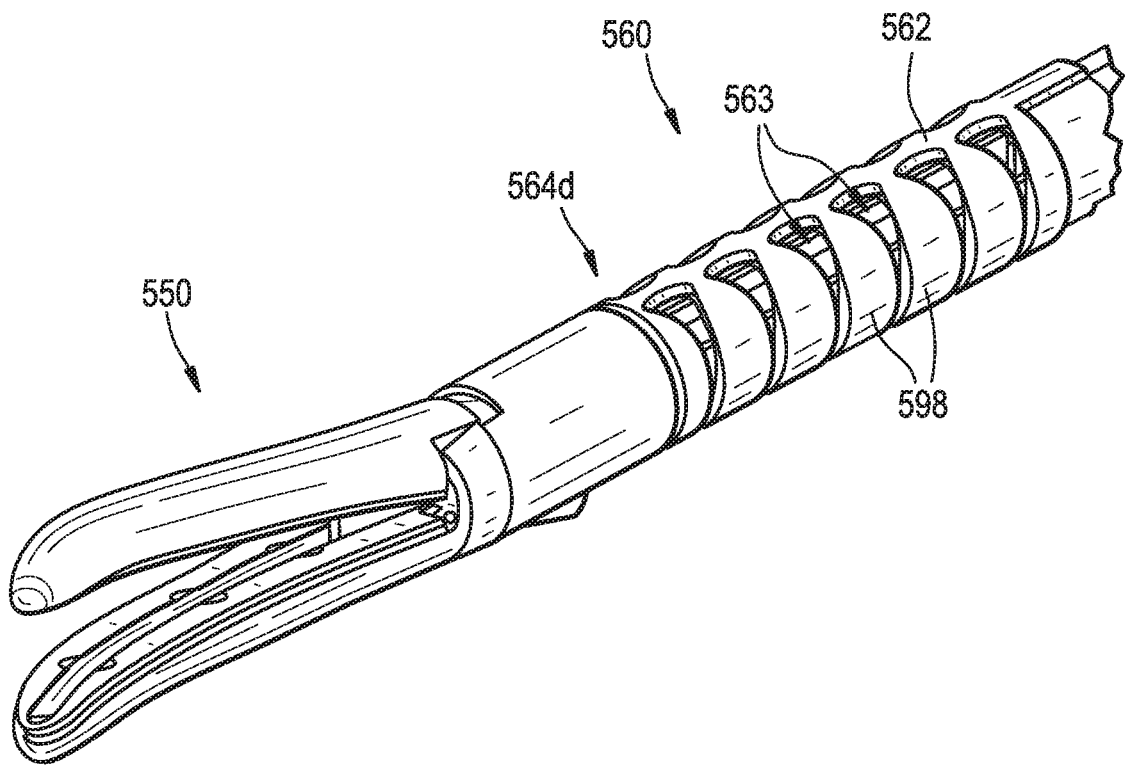
FIG. 22 is an isometric view of another exemplary embodiment of a distal articulation end of a surgical device, the distal articulation end including an end effector and an articulation joint having an outer sleeve and an inner guide.
Figure 23:
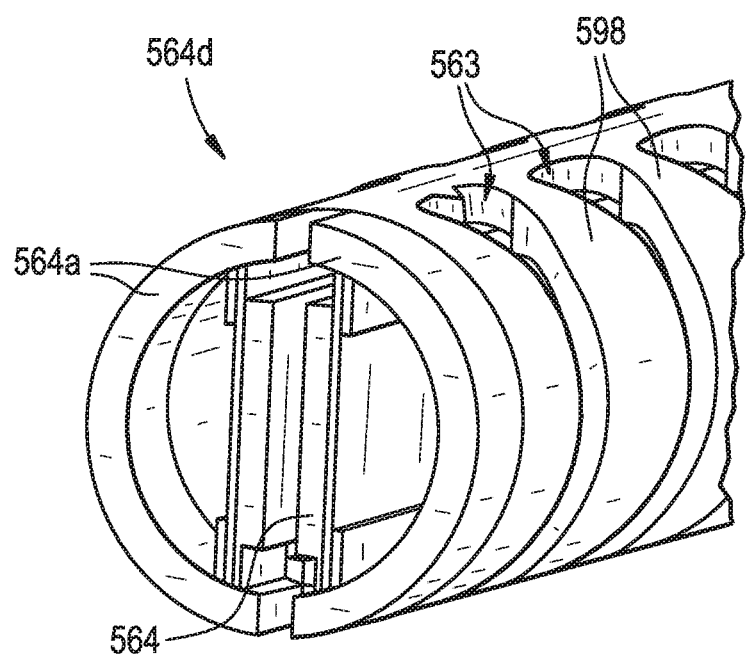
FIG. 23 is a detailed front perspective view of a distal end of the outer sleeve and the inner guide of FIG. 22.
Figure 24:
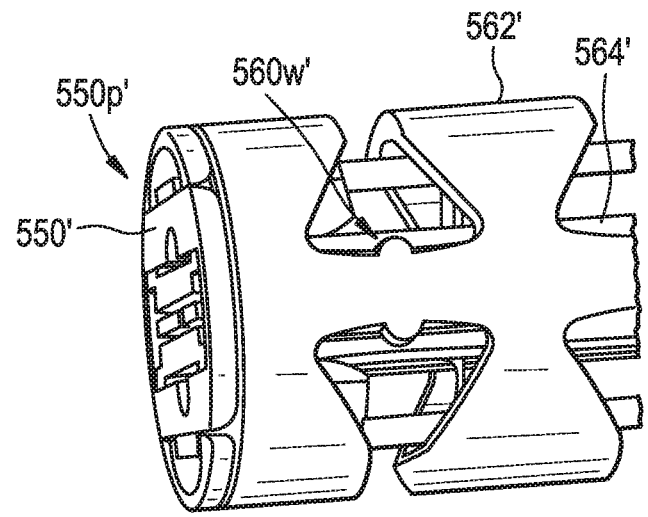
FIG. 24 is a detailed side perspective view of a distal end of still another exemplary embodiment of an articulation joint having an outer sleeve and an inner guide.
Figure 25:
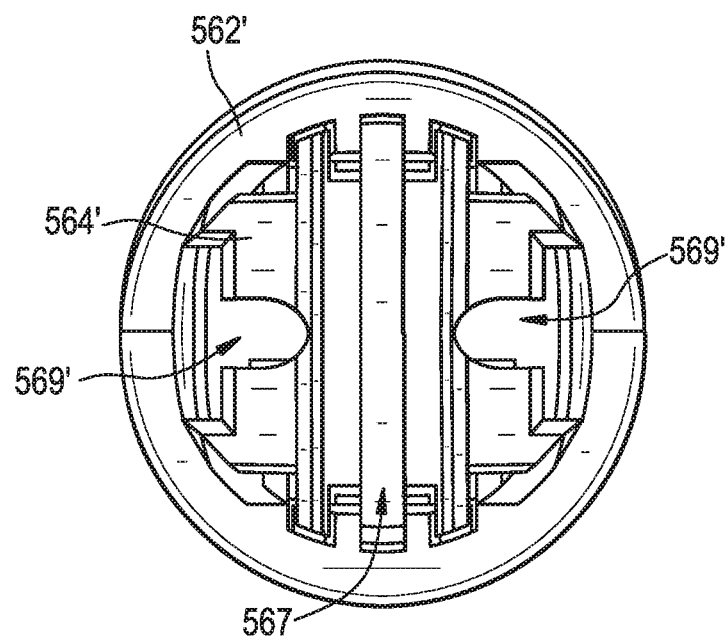
FIG. 25 is a front perspective view of the distal end of the outer sleeve and the inner guide of FIG. 24.

Still another exemplary embodiment of an articulation joint 560 is illustrated in FIGS. 22-23, with FIGS. 24 and 25 showing a slightly different version of a similar articulation joint. FIG. 22 shows a distal end of a surgical device, and includes an articulation joint 560 having both an outer sleeve 562 having slots 563 formed therein and an inner guide 564. The configuration of the articulation joint 560 of this device differs from other configurations in that the inner guides 564 include a distal end 564 d having arches 564a formed thereon. As shown, the arches 564a are formed to be complementary to the arches 598 of the outer sleeve 562 such that outer surfaces of the arches 564 a are substantially flush with the outer surface of the outer sleeve 562. The configuration of the outer sleeve 562 can be a singular structure that is similar in nature to a configuration would be if two cage members were coupled together to form a unitary piece. In other embodiments, a tubular member can be used to associate two cage members together, or outer sleeves of the nature provided for in other embodiments can also be used. In the illustrated embodiment, the arches 564a can be mated together using any number of techniques provided for herein or otherwise known to those skilled in the art, including ultrasonic welding. A proximal end of the end effector 550 and the arches 564a can be configured to mate together using any number of techniques provided for herein or otherwise known to those skilled in the art.

FIG. 24 illustrates one example of a technique that can be used to mate a similarly designed outer sleeve 562' to a similarly designed inner guide 564', although the illustrated inner guide 564' does not include the arches 564a described above with respect to FIGS. 22 and 23. The techniques illustrated in FIGS. 24 and 25 can be used in conjunction with the mating techniques described with respect to FIGS. 22 and 23. A portion disposed at the distal end of the articulation joint is a proximal end 550p' of the end effector 550'. As shown, one or more welds 560w' can be formed between the outer sleeve 562' and the inner guide 564'. Additionally, or alternatively, inner surfaces of the outer sleeve 562' can be adapted to receive outer surfaces of the inner guide 564', as shown in FIG. 25 by way of channels of the outer sleeve 562' receiving ends of the inner guide 564'. As shown in FIG. 25, the resulting combination includes a central channel 567' configured to receive a cutting mechanism and/or a closure band, and first and second channels 569' configured to receive articulation bands. The first and second channels 569' include both a substantially rectangular portion for receiving the articulation bands, but also include a substantially cylindrical portion for receiving a component such as a wire for powering the electrodes. Of course, many other configurations are possible, depending, at least in part, on the size and shape of the other components of the device with which the articulation joint is used and the type of procedure being performed.

Use of Surgical Device

In use, as described with respect to the surgical device 10, the surgical device 10 can be disposed in a cannula or port and disposed at a surgical site. Placement of the end effector 50 at the surgical site can be achieved by manipulating the handle portion 20, and thus the shaft 40 and the end effector 50 coupled thereto, across six degrees of freedom—side-to-side, up-and-down, and in-and-out from the perspective of the user facing a body in which the surgical site is disposed—and utilizing some of the features of the device 10, including but not limited to the rotating knob 32 to rotate the shaft 40 and end effector 50 and the actuating lever 28 to articulate the end effector 50. For example, the articulation lever 28 can be rotated to the right (into the page) to advance the left articulation band 80 distally with respect to the inner guide 64 and the channel 69 in which it is disposed and retract the right articulation band 82 proximally with respect to the inner guide 64 and the channel 69 in which it is disposed, thus causing the end effector 50 to rotate to the right (into the page) with respect to the central longitudinal axis L when viewed from above. Likewise, rotating the articulation lever 28 to the left (out of the page) can advance the right articulation band 82 distally with respect to the inner guide 64 and the channel 69 in which it is disposed and retract the left articulation band 80 proximally with respect to the inner guide 64 and the channel 69 in which it is disposed, thus causing the end effector 50 to rotate to the left (out of the page) with respect to the central longitudinal axis L when viewed from above.

As the articulation lever 28 is manipulated to articulate the end effector 50, the inner guide 64 can flex to allow for the articulation without pinching the articulation bands 80, 82, the cutting mechanism 90, and the closure band 84 to prevent their distal and proximal movement, even when the articulation joint 60, and thus the end effector 50, is in the fully-articulated configuration. The inner guide 64 can also distribute throughout its elongate body 66 any load resulting from the jaws 52, 54 being clamped together, as they typically are when the device 10 is being passed through the body to the surgical site. Likewise, the outer sleeve 62 is able to be flexible throughout the course of articulating, no matter the articulated configuration of the articulation joint 60 and the end effector 50.

After appropriate positioning has been achieved such that a tissue to be cut is located between the jaws 52, 54 of the surgical device 10, or alternatively the tissue has been manipulated to be between the jaws, the trigger 24 can be pulled toward the stationary handle 26 to distally advance the closure band 84 and cutting mechanism 90 through the channel 67 formed in the inner guide 64. As these two components 84 and 90 advance distally, the closure band 84 can slide along the opposed slots 58 formed in the upper jaw 52 to advance the upper jaw 52 towards the lower jaw 54. The cutting mechanism 90 can remain proximal of a location in the jaws 52, 54 in which the tissue is disposed so that any cutting does not occur until after the jaws are in their closed position. Depending on how the internal components of the handle portion 20 are configured, a completion of a stroke of the trigger 24 may complete the closing of the jaws 52, 54 and a second stroke may be used to perform the cutting of the tissue. Alternatively, the jaws 52, 54 may achieve their closed position during an intermediate portion of the stroke of the trigger 24 towards the stationary handle 26 such that continued advancement of the trigger 24 towards the stationary handle 26 can cause the cutting mechanism 90 to advance distally through at least a portion of the jaws 52, 54 to cut the tissue disposed between the jaws 52, 54. In some embodiments, once the trigger 24 has been advanced as close to the stationary handle 26 as permitted by the design, referred to herein as a fully-compressed position, the cutting mechanism 90 is advanced as distally as it can with respect to the jaws 52, 54. The action of closing the jaws 52, 54 can cause one of the jaws, e.g., the upper jaw 52, to apply a force of load to the other jaw, e.g., the lower jaw 54, and more generally to the instrument 10. The inclusion of the inner guide 64, however, allows that force or load to be displaced through the elongate body 66, which thus minimizes and/or prevents the jaws 52, 54 from becoming displaced with respect to the articulation joint 60 and/or the outer elongate shaft 40. Further, when the jaws 52, 54 are closed, the button 30 can be pressed to initiate power being supplied to the electrode 56, via the wire 30, to supply energy to the grasped tissue for sealing or coagulating it.

As the trigger 24 is returned to its initial position, i.e., as it moves away from the stationary handle 26, the cutting mechanism 90 and closure band 84 can retract until the initial position is reached. In the initial position, the cutting mechanism 90 is disposed proximal of the end effector 50 and the closure band 84 is disposed at the proximal end of the slots 58 so that the jaws 52, 54 are in the open configuration. Furthermore, the trigger 24 can be located at the initial position, at the fully-compressed position, or at any position therebetween, and it remains operable no matter how articulated the end effector 50 is due to the configuration of the articulation joint 60. Thus, even when the articulation joint 60, and thus the end effector 50, are in the fully articulated configuration, the trigger 24 can be disposed at any location including and between the initial position and the fully-compressed configuration.

A person skilled in the art will recognize that many other methods for operating a surgical device of the nature provided for herein or otherwise derivable from the present disclosure are possible in view of the present disclosures. Thus, the described method is in no way limiting with respect to how the described articulation joint can be used in a surgical device to allow for articulation of an end effector of a surgical device while allowing for other components, e.g., a cutting mechanism, a closure band, articulation mechanisms, and a wire, to be useable no matter how articulated the end effector is with respect to an elongate shaft of the surgical device. To the extent methods for operating surgical devices existed prior to the present disclosure, the disclosure articulation joint and related components can be incorporated into such devices and used to provide for enhanced performance that allows the various components to work at any conceivable degree of articulation.

Further, it is understood that the features provided for in one embodiment of an articulation joint, and more broadly a surgical device, can be incorporated into the other embodiments provided for herein without departing from the spirit of the present disclosure. The disclosure, in view of a person having skill in the art, allows for various features to be utilized in the various configurations of articulation joints and surgical devices disclosed herein or otherwise derivable therefrom. By way of non-limiting example, various formations of outer sleeves, including their slots, cage members, etc., and inner guides, including their channels, ribs, stiffening elements, etc., can be adapted for use across the various embodiments described, or in similar devices known to those skilled in the art.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the disclosure based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. A surgical device, comprising:
   a housing;
   an elongate shaft extending distally from the housing;
   an articulation joint coupled to a distal end of the elongate shaft, the articulation joint comprising:
      an outer sleeve having a plurality of radially-extending slots formed therein; and
      an inner guide disposed within the outer sleeve,
      wherein each of the outer sleeve and the inner guide is coupled to the elongate shaft, and the combination thereof forming at least three separate channels that each extend a length of the inner guide, the three separate channels including a first channel configured to receive an actuation member that extends from the housing, through the elongate shaft, and into the articulation joint, a second channel configured to receive a first articulation arm that extends from the housing, through the elongate shaft, and into the articulation joint, and a third channel configured to receive a second articulation arm that extends from the housing, through the elongate shaft, and into the articulation joint; and
   an end effector coupled to the articulation joint and configured to be actuated by the actuation member and articulated by the first and second articulation arms.

2. The surgical device of claim 1, wherein the inner guide further comprises:
   an elongate body having the first channel formed therethrough, the elongate body having a plurality of first ribs disposed along a length of a first outer surface of the body and a plurality of second ribs disposed along a length of a second outer surface of the body, the plurality of second ribs being disposed on an opposite side of the body than the plurality of first ribs, with the plurality of first ribs and a portion of the outer sleeve defining at least a portion of the second channel and the plurality of second ribs and another portion of the outer sleeve defining at least a portion of the third channel.

3. The surgical device of claim 2, further comprising:
   a first stiffening element coupled to a first inner wall of the elongate body; and a second stiffening element coupled to a second inner wall of the elongate body, the first and second inner walls being opposed to each other on opposite sides of the first channel such that the first and second stiffening elements are also opposed to each other on opposite sides of the first channel.

4. The surgical device of claim 3, wherein a distal end of each of the first and second stiffening elements extends distally beyond a distal terminal end of the elongate body of the inner guide, the distal ends of the first and second stiffening elements being coupled to the end effector.

5. The surgical device of claim 3, wherein each of the first and second stiffening elements comprises metal.

6. The surgical device of claim 2,
wherein one or more of the plurality of first ribs comprises opposed first and second wings, the first and second wings defining a space therebetween that is part of the second channel, and
wherein one or more of the plurality of second ribs comprises opposed first and second wings, the first and second wings defining a space therebetween that is part of the third channel.

7. The surgical device of claim 1,
wherein the plurality of radially-extending slots of the outer sleeve further comprises a plurality of rows of radially-extending slots with each row being disposed at a different location along a length of the outer sleeve, and each row including at least a first radially-extending slot and a second radially-extending slot, and
wherein a distance between adjacent, opposed terminal ends of the first radially-extending slot and the second radially-extending slot is constant across the length of the outer sleeve.

8. The surgical device of claim 1,
wherein the plurality of radially-extending slots of the outer sleeve further comprises a plurality of rows of radially-extending slots with each row being disposed at a different location along a length of the outer sleeve,
wherein a distance between adjacent, opposed terminal ends of a first one of the plurality of radially-extending slots and a second one of the plurality of radially-extending slots at a proximal end of the plurality of rows of slots is greater than a distance between adjacent, opposed terminal ends of a third one of the plurality of radially-extending slots and a fourth one of the plurality of radially-extending slot at an intermediate section of the plurality of rows, and
wherein a distance between adjacent, opposed terminal ends of a fifth one of the plurality of radially-extending slots and a sixth one of the plurality of radially-extending slots at a distal end of the plurality of rows of slots is greater than the distance between the adjacent, opposed terminal ends of the third one of the plurality of radially-extending slots and the fourth one of the plurality of radially-extending slots at the intermediate section of the plurality of rows.

9. The surgical device of claim 8, wherein the terminal ends of each of the first, second, third, fourth, fifth, and sixth ones of the plurality of radially-extending slots are curved towards at least one of a proximal end and a distal end of the outer sleeve.

10. The surgical device of claim 1, wherein the outer sleeve further comprises:
a tubular body having a proximal portion, an intermediate portion, and a distal portion, with the intermediate portion having opposed support arms that extend between the proximal and distal portions;
a first cage member in which a portion of the plurality of radially-extending slots are formed, the first cage member engaging the opposed support arms and being coupled to the inner guide; and
a second cage member in which another portion of the plurality of radially-extending slots are formed, the second cage member engaging the opposed support arms, being disposed on an opposite side of the opposed support arms than the first cage member, and being coupled to the inner guide.

11. The surgical device of claim 1, wherein one of the second and third channels is further configured to receive a wire that extends from the housing, through the elongate shaft, into the articulation joint, and to the end effector to provide power to the end effector.

12. The surgical device of claim 1, wherein the end effector further comprises a first jaw and a second jaw configured to move relative to one another between an open position in which the jaws are spaced a distance apart from one another and a closed position in which the jaws are configured to grasp tissue therebetween.

13. The surgical device of claim 12, further comprising a cutting blade disposed in the first channel and configured to advance therethrough and through the first and second jaws to cut tissue grasped therebetween.

14. The surgical device of claim 1, further comprising an insulative adapter disposed between the elongate shaft and the articulation joint to couple the articulation joint to the elongate shaft, the insulative adapter being configured to electrically isolate the end effector from the elongate shaft.

15. The surgical device of claim 1, further comprising a first stiffening element and a second stiffening element, the first and second stiffening elements being opposed to each other on opposite sides of the first channel, and a distal end of each of the first and second stiffening elements extending distally beyond a distal terminal end of an elongate body of the inner guide.

16. The surgical device of claim 1, wherein the first channel extends an entire length of the inner guide and is enclosed on all sides by the inner guide.

17. The surgical device of claim 1, wherein the inner guide includes a first body and a second body that is coupled to the first body to form the inner guide;
the first body includes a female coupling member; and
the second body includes a male coupling member that is coupled to the female coupling member so as to couple the first and second bodies together to form the inner guide.

18. The surgical device of claim 17, wherein the first channel is defined by facing external surfaces of the first body and the second body;
the second channel is defined by the first body on a first side of the first channel laterally away from the second body; and
the third channel is defined by the second body on a second, opposite side of the first channel laterally away from the first body.

19. The surgical device of claim 17, further comprising:
a first stiffening element attached to a surface of the first body such that the first stiffening element is in a fixed position relative to the first body and extends longitudinally along the first body; and
a second stiffening element attached to a surface of the second body such that the second stiffening element is in a fixed position relative to the second body and extends longitudinally along the second body.

20. A surgical device, comprising:
a housing;
an elongate shaft extending distally from the housing;
an articulation joint coupled to a distal end of the elongate shaft, the articulation joint including an inner guide and an outer sleeve disposed radially outward from the inner guide, the outer sleeve having a plurality of rows of radially-extending slots formed therein;
a first articulation band extending from the housing, through the elongate shaft, and into the articulation joint, wherein the outer sleeve defines at least a portion of a first outer channel for receiving the first articulation band;
a second articulation band, on an opposite side of the inner guide than the first articulation band and extending from the housing, through the elongate shaft, and into the articulation joint, wherein the outer sleeve defines at least a portion of a second outer channel for receiving the second articulation band;
a jaw assembly coupled to the articulation joint and each of the first and second articulation bands, the jaw assembly having a first jaw and a second jaw pivotally coupled together to open and close to grasp tissue therebetween, the jaw assembly being configured to be articulated by the first and second articulation bands between a straight configuration and a fully-articulated configuration; and
a cutting blade configured to advance through at least a portion of the first and second jaws to cut tissue grasped therebetween,
wherein the inner guide comprises:
 an inner channel formed therein and entirely closed thereby, the inner channel being configured to receive the cutting blade;
 opposed stiffening elements disposed on opposed sides of a distal portion of the inner channel, the stiffening elements being fixedly attached to inner walls of the inner guide that define the inner channel;
 a plurality of first ribs disposed along a length of a first outer surface of the inner guide, the plurality of first ribs defining at least a portion of the first outer channel; and
 a plurality of second ribs disposed along a length of a second outer surface of the inner guide, the plurality of second ribs being disposed on an opposite side of the inner guide than the plurality of first ribs, and the plurality of second ribs defining at least a portion of the second outer channel; and
wherein the articulation joint is configured to allow the cutting blade to advance and retract when the jaw assembly is in any configuration between and including the straight configuration and the fully-articulated configuration.

21. The surgical device of claim 20,
wherein each row of the plurality of rows of radially-extending slots is disposed at a different location along a length of the outer sleeve, and each row includes at least a first slot and a second slot, and
wherein a distance between adjacent, opposed terminal ends of the first slot and the second slot is constant across the length of the outer sleeve.

22. The surgical device of claim 20,
wherein each row of the plurality of rows of radially-extending slots being disposed at a different location along a length of the outer sleeve, and each row including at least a first slot and a second slot,
wherein a distance between adjacent, opposed terminals ends of the first and second slots at a proximal end of the plurality of rows of slots is greater than a distance between adjacent, opposed terminal ends of the first and second slots at an intermediate section of the plurality of rows, and
wherein a distance between adjacent, opposed terminal ends of the first and second slots at a distal end of the plurality of rows of slots is greater than the distance between the opposed terminal ends of the first and second slots at the intermediate section of the plurality of rows.

23. The surgical device of claim 22, wherein terminal ends of the first and second slots of the plurality of rows are curved towards at least one of a proximal end and a distal end of the outer sleeve.

24. The surgical device of claim 20, wherein the outer sleeve further comprises:
 a tubular body having a proximal portion, an intermediate portion, and a distal portion, with the intermediate portion having opposed support arms that extend between the proximal and distal portions;
 a first cage member having a plurality of slots formed therein, the first cage member engaging the opposed support arms and being coupled to the inner guide; and
 a second cage member having a plurality of slots formed therein, the second cage member engaging the opposed support arms, being disposed on an opposite side of the opposed support arms than the first cage member, and being coupled to the inner guide.

25. The surgical device of claim 20, wherein each of the first and second stiffening elements comprises metal.

26. The surgical device of claim 20, further comprising an insulative adapter disposed between the elongate shaft and the articulation joint to couple the articulation joint to the elongate shaft, the insulative adapter being configured to electrically isolate the jaw assembly from the elongate shaft.

27. The surgical device of claim 20, wherein a distal end of each of the opposed stiffening elements extends distally beyond a distal terminal end of an elongate body of the inner guide to which the opposed stiffening elements are coupled, the distal ends of the opposed stiffening elements being coupled to the jaw assembly.

* * * * *